United States Patent
Dalence et al.

(10) Patent No.: US 11,680,054 B2
(45) Date of Patent: Jun. 20, 2023

(54) BRONCHODILATING HETERO-LINKED AMIDES

(71) Applicant: Arcede Pharma AB, Lund (SE)

(72) Inventors: Maria Dalence, Lund (SE); Martin Johansson, Helsingborg (SE); Viveca Thornqvist Oltner, Landskrona (SE); Jörgen Toftered, Lund (SE); David Wensbo, Lund (SE)

(73) Assignee: Arcede Pharma AB, Lund (SE)

( * ) Notice: Subject to any disclaimer, the term of this patent is extended or adjusted under 35 U.S.C. 154(b) by 253 days.

(21) Appl. No.: 17/255,264

(22) PCT Filed: Jul. 5, 2019

(86) PCT No.: PCT/SE2019/050674
§ 371 (c)(1),
(2) Date: Dec. 22, 2020

(87) PCT Pub. No.: WO2020/009653
PCT Pub. Date: Jan. 9, 2020

(65) Prior Publication Data
US 2021/0139455 A1 May 13, 2021

(30) Foreign Application Priority Data
Jul. 6, 2018 (SE) .................................. 1850859-8

(51) Int. Cl.
| | |
|---|---|
| *C07D 401/12* | (2006.01) |
| *A61P 11/08* | (2006.01) |
| *A61K 31/4725* | (2006.01) |
| *A61K 45/06* | (2006.01) |
| *C07D 401/14* | (2006.01) |

(52) U.S. Cl.
CPC ........ *C07D 401/12* (2013.01); *A61K 31/4725* (2013.01); *A61K 45/06* (2013.01); *A61P 11/08* (2018.01); *C07D 401/14* (2013.01)

(58) Field of Classification Search
CPC ............... C07D 401/12; C07D 401/14; A61K 31/4725; A61K 45/06; A61P 11/06; A61P 11/08
See application file for complete search history.

(56) References Cited

U.S. PATENT DOCUMENTS

| | | |
|---|---|---|
| 5,158,959 A | 10/1992 | Geiger et al. |
| 6,838,465 B2 | 1/2005 | Yamada et al. |
| 2006/0040254 A1 | 2/2006 | Skogvall |
| 2010/0256101 A1 | 10/2010 | Dalence et al. |

FOREIGN PATENT DOCUMENTS

| | | |
|---|---|---|
| WO | 2008095852 | 8/2008 |
| WO | 2009007418 A1 | 1/2009 |
| WO | 2009007419 | 1/2009 |
| WO | 2017152032 | 9/2017 |

OTHER PUBLICATIONS

Skogvall, S., Berglund, M., Dalence-Guzmán, M. F., Svensson, K., Jönsson, P., Persson, C. G. A and Sterner, O. Pulmonary Pharmacology and Therapeutics, vol. 20:3, 2007, p. 273-280.
Gunthorpe, M. J., Neurpharmacology, 2004, 46, 133.
Pulmonary Pharmacology & Therapeutics, 2007, 21(1), 125-133.
Friedman et al, Clinical Cornerstone, 2003, 5, 45-51.
Tomaki, M. et al, Pulmonary Pharmacology & Therapeutics, 2007, 20, 596-605.
Aldonyte, R. et al, Respiratory Research, 2003, http://respiratory-research.com/content/4/1/11.
Marian, E. et al, 2006, 129, 1523-1530.
Profita, M. et al, Allergy, 2005, 60, 1361-1369.
Segger, J.S. et al, Chest, 1991, 99, 289-291.
Matsuyama, W. et al, Chest, 2005, 128, 3817-3827.
M.F. Fitzgerald and J.C. Fox, Drug Discovery Today, 2007, 12 (11/12), p. 472-478.
Toftered et al., SYNLETT, 2004, 2517-2520.
Dunn et al., Org. Proc. Res. Dev., 2005, 9, 956-961.
Hall et al., Bioorg. Med. Chem, 2005, 13, 1409-1413.
Yokoyama et al., J Org Chem, 1999, 64, 611-617.
Stokker et al., Tetrahedron Lett, 1996, 37, 5453-5456.
Bobbit et al., J Org Chem, 1965, 30, 2247-2250.
Bobbit et al., J Org Chem, 1968, 33, 856-858.
Okano et al., Tetrahedron, 2006, 128, 7136-7137.
Bioorganic & Medicinal Chemistry Letters 20 (2010) 4999-5003.
Traves, L.S. et al, Thorax, 2002, 57, 590-595.
Mahmutovic-Persson et al Int Immunopharmacol Jul. 2012, vol. 13 No. 3 pp. 292-300.
Mahmutovic-Persson Lund University Faculty of Medicina, 2016 pp. 49, 60.
Dalence-Guzmán et al; Bioorg. Med Chem Lett Sep. 2010 vol. 20 No. 17 pp. 4999-5003.

*Primary Examiner* — Kortney L. Klinkel
*Assistant Examiner* — Padmaja S Rao
(74) *Attorney, Agent, or Firm* — Renner, Otto, Boisseile & Sklar, LLP

(57) ABSTRACT

The invention relates to novel molecules having the general formula (I), and which molecules are useful to treat a disorder or disease characterized by bronchoconstriction, e.g. COPD and asthma inflammation and/or vasoconstriction, e.g. hypertension.

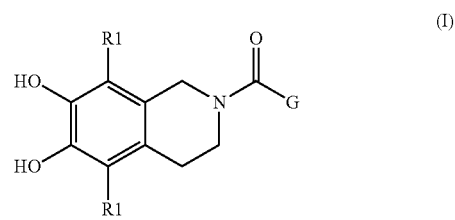

20 Claims, No Drawings

BRONCHODILATING HETERO-LINKED AMIDES

This application is a national phase of International Application No. PCT/SE2019/050674 filed Jul. 5, 2019 and published in the English language, which claims priority to Swedish Application No. 1850859-8 filed Jul. 6, 2018, both of which are hereby incorporated herein by reference.

TECHNICAL FIELD

The present invention relates to novel dual acting compounds with bronchorelaxing and antiinflammatory properties, pharmaceutical compositions comprising such compounds, and a method of treating or alleviating conditions accompanied by bronchoconstriction and/or inflammation of the respiratory tract, and/or vasoconstriction, by use of such compounds.

BACKGROUND

Asthma and chronic obstructive pulmonary disease (COPD) are diseases affecting the respiratory system, which millions of people suffer from. These diseases are today regarded as inflammatory diseases and the symptoms comprise constriction of the airways. Common treatment of the associated bronchoconstriction involves use of beta-agonists, such as terbutalin and formoterol, and anticholinergics, such as ipratropium bromide and tiotropium bromide.

Hypertension, i.e. high blood pressure, increases the risk of stroke, heart attacks, heart failure and kidney disease. Medications presently used for the treatment of hypertension include the administration of beta-blockers, calcium channel blockers, diuretics, angiotensin-converting enzyme inhibitors and angiotensin II receptor antagonists. Vasoconstriction results in an increase in the blood pressure.

The treatments for prevention or reduction of bronchoconstricion, inflammation, such as inflammation of the respiratory tract, and vasoconstriction are in many ways insufficient and there is a need for alternative treatments.

Corticosteroids have been used to treat the inflammation, such as the inflammation seen in the airways of patients suffering from asthma. Such treatment is fairly effective in the case of asthma, although the inflammation may persist, at least to some extent. Further, corticosteroids are also used to treat the inflammation seen in the airways of patients suffering from COPD. The effect on the inflammation, in the case of COPD, is much less pronounced, if any effect at all is seen.

The tetrahydroisoquinoline (2E)-1-(5,8-dichloro-6,7-dihydroxy-1,2,3,4-tetrahydroisoquinolin-2-yl)-3-[6-(trifluoromethyl)pyridin-3-yl]prop-2-en-1-one has been described as a dual acting compound with highly efficacious bronchodilating properties combined with anti-inflammatory properties (cf. Bioorganic & Medicinal Chemistry Letters 20 (2010) 4999-5003; and International Immunopharmacology 13 (2012) 292-300). Because of this unique profile, (2E)-1-(5,8-dichloro-6,7-dihydroxy-1,2,3,4-tetrahydroisoquinolin-2-yl)-3-[6-(trifluoro-methyl)pyridin-3-yl]prop-2-en-1-one is a potential new drug for the treatment of COPD and severe asthma, as reported in the art.

However, (2E)-1-(5,8-dichloro-6,7-dihydroxy-1,2,3,4-tetrahydroisoquinolin-2-yl)-3-[6-(trifluoro-methyl)pyridin-3-yl]prop-2-en-1-one contains an α,β-unsaturated acrylamide moiety which potentially could act as a non-specific Michael acceptor and cause unwanted toxicities. Therefore, a compound with a similar pharmacological profile, but without the structural liability would be desirable. Further, in the cited art, a number of related compounds, as well as a 1,8-naphthyridine derivative (i.e. N-(4-tert-butylbenzyl)-2-methyl-1,8-naphthyridine-3-carboxamide), are also disclosed. Still, it would of interest to provide compounds having a longer duration of action in the lungs, while still being rapidly eliminated systemically. Especially, it would be of interest to provide compounds with high bronchodilatating effect in vivo, as the effect in in vivo models, not necessarily may be mirroring the in vitro effect.

SUMMARY

The present invention seeks to mitigate, alleviate, circumvent or eliminate at least one, such as one or more, of the above-identified deficiencies.

Accordingly there is provided, according to one aspect of the invention, a compound, which may be represented with the general formula (I)

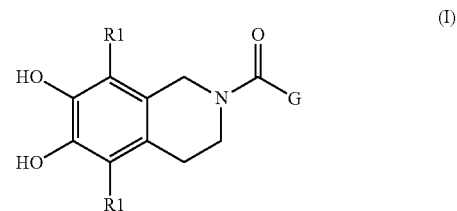

wherein R1 is independently selected from H, fluoro, chloro and bromo; G is selected from G1 to G3, wherein R2 is independently selected from H and C1-2 alkyl, Y is S or NR3, and (het)Ar is a monocyclic aromatic ring; said ring being substituted with a maximum of "n" independently selected substituent(s) R4 at any substitutable ring atom, wherein "n" represents an integer number;

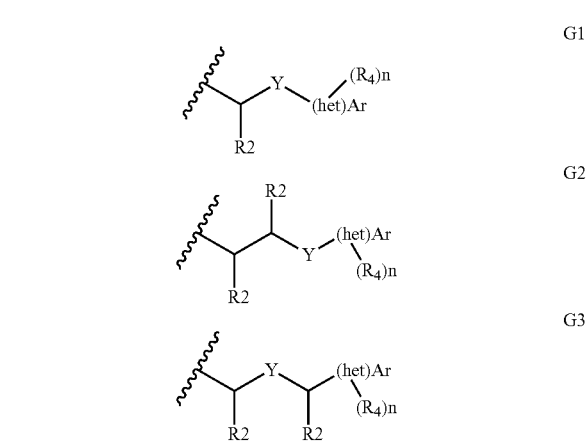

The integer number "n" is 0 (zero) to 2 (two); R3 is selected from H, C1-5 alkyl, C2-5 fluoroalkyl, C1-3 alkyleneOC0-5 alkyl, C0-3 alkyleneNHC0-3 alkyl, C0-3 alkyleneN(C1-5 alkyl)2, in which the C1-5 alkyl may be the same or different, (CO)C1-5 alkyl, (CO)N(C0-5 alkyl)2, in which the C0-5 alkyl may be the same or different, and (CO)OC1-5 alkyl; Two R2 or R2 and R3, if present, may optionally be connected to each other, or R2 or R3 may be connected to the carbon- or nitrogen-atom onto which the other R2 or R3 is attached if the other R2 or R3 is hydrogen, by a bond replacing a hydrogen atom in each substituent to form part of a 5-membered or a 6-membered ring; R4 is independently selected from C1-5 alkyl, C1-5 fluoroalkyl, halo, OH, NH2, C0-C3 alkylene phenyl, C0-C3 alkylene heteroaryl, C0-1 alkylene cyano, C0-3 alkyleneOC0-5 alkyl, C0-3 alkyleneNHC0-3 alkyl, C0-3 alkyleneN(C1-5 alkyl)2, in which the C1-5 alkyl may be the same or different, N(C4-5 alkylene), N-morpholino, CO2H, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)2, in which the C1-5 alkyl may be the same or different, CO-3 alkyleneC(O)N(C4-5 alkylene) and (CO)NH2; as a free base, an acid in its non-charged protonated form or a pharmaceutically acceptable salt, solvate or solvate of a salt thereof and as a pure stereoisomer, a racemic-, diastereomeric- or scalemic mixture;

According to another aspect of the invention there is provided a pharmaceutical composition, which may comprise a compound according formula (I) and at least one pharmaceutically acceptable carrier.

According to another aspect of the invention a compound according to formula (I) or a pharmaceutical composition as disclosed above may be used in therapy.

According to another aspect of the invention, a compound according to formula (I) or a pharmaceutical composition as disclosed above may be used to prevent and/or treat a disease or condition characterized by bronchoconstriction of the respiratory apparatus. Such diseases or conditions characterized by bronchoconstriction of the respiratory apparatus may be asthma, chronic obstructive pulmonary disease, chronic bronchitis, emphysema, bronchiectasis, cystic fibrosis, bronchiolitis and bronchopulmonary dysplasia.

According to another aspect of the invention, a compound according to formula (I) or a pharmaceutical composition as disclosed above may be used to prevent and/or treat a disease or condition characterized by inflammatory conditions of the respiratory apparatus. Such diseases or conditions characterized by inflammatory conditions of the respiratory apparatus may be asthma, chronic obstructive pulmonary disease, chronic bronchitis, emphysema, bronchiectasis, cystic fibrosis, bronchiolitis and bronchopulmonary dysplasia.

According to another aspect of the invention there is provided method of preventing and/or treating a disease or condition characterized by bronchoconstriction of the respiratory apparatus and/or inflammatory conditions of the respiratory apparatus. Such a method comprises the step of administering, to a mammal, including man in need of such prevention and/or treatment, a therapeutically effective amount of a compound according formula (I).

According to another aspect of the invention a compound according to formula (I) or a pharmaceutical composition as disclosed above may be used to prevent and/or treat a disease or condition characterized by systemic or respiratory vasoconstriction. Additionally, a method of preventing and/or treating a disease or condition characterized by systemic or respiratory vasoconstriction, may comprise the step of administering, to a mammal, including man in need of such prevention and/or treatment, a therapeutically effective amount of a compound according to formula (I).

Further, advantageous features of various embodiments of the invention are defined in the dependent claims and within the detailed description below.

DETAILED DESCRIPTION OF EXAMPLE EMBODIMENTS

Definitions

In the context of the present application and invention, the following definitions apply:

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(CO alkyl)2" is equivalent to "NH2" (amino).

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" "C1-6 alkylene" denotes alkylenyl or alkylene having 1, 2, 3, 4, 5 or 6 carbon atoms. When the specific number denoting the alkylenyl or alkylene-group is the integer 0 (zero), a bond is intended to link the groups onto which the alkylenyl or alkylene-group is substituted. For example, "NH(CO alkylene)NH2" is equivalent to "NHNH2" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "H2N(C2 alkylene)NH2", "H2N (C3 alkylene)NH2", "N(C4 alkylene)", "N(C5 alkylene)" and "N(C2 alkylene)2NH" is equivalent to 1,2-diamino ethane, 1,3-diamino propane, pyrrolidinyl, piperidinyl and piperazinyl, respectively.

Examples of alkyl include, but are not limited to, methyl, ethyl, n-propyl, i-propyl, n-butyl, i-butyl, sec-butyl, t-butyl, pentyl, and hexyl.

Examples of alkylene or alkylenyl include, but are not limited to, methylene, ethylene, propylene, and butylene.

As used herein, "alkoxy" or "alkyloxy" is intended to mean an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to any of the carbons of the corresponding alkyl, alkylene and alkoxy-groups are replaced by fluoro. Examples of fluoroalkyl include, but are not limited to, trifluoromethyl, difluoromethyl, fluoromethyl, 2,2,2-trifluoroethyl, 2-fluoroethyl and 3-fluoropropyl. Examples of fluoroalkylene include, but are not limited to, difluoromethylene, fluoromethylene, 2,2-difluorobutylene and 2,2,3-trifluorobutylene. Examples of fluoroalkoxy include, but are not limited to, trifluoromethoxy, 2,2,2-trifluoroethoxy, 3,3,3-trifluoropropoxy and 2,2-difluoropropoxy.

As used herein, the term "substitutable" refers to an atom to which a hydrogen may be covalently attached, and to which another substituent may be present instead of the hydrogen. A non-limiting example of substitutable atoms include the carbon-atoms of pyridine. The nitrogen-atom of pyridine is not substitutable according to this definition. Further, according to the same definition, the imine nitrogen at position 3 in imidazole is not substitutable, while the amine nitrogen at position 1 is.

As used herein, the term "aryl" refers to a ring structure, comprising at least one aromatic ring, made up of from 5 to 14 carbon atoms. Ring structures containing 5, 6, 7 and 8 carbon atoms would be single-ring aromatic groups, for example phenyl. Ring structures containing 8, 9, 10, 11, 12, 13, or 14 would be polycyclic, for example naphthyl. The aromatic ring can be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl groups include monocyclic and bicyclic (e.g., having 2 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

Embodiments of the Invention

According to one embodiment of the present invention there is disclosed a compound according to the general formula (I),

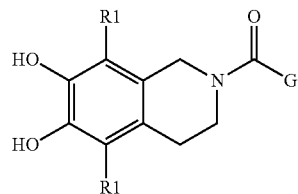

wherein R1 is independently selected from H, fluoro, chloro and bromo;

G is selected from G1 to G3, wherein R2 is independently selected from H and C1-2 alkyl, Y is selected from S and NR3, and (het)Ar is a monocyclic aromatic ring; said ring being substituted with a maximum of "n" independently selected substituent(s) R4 at any substitutable ring atom, wherein "n" represents an integer number;

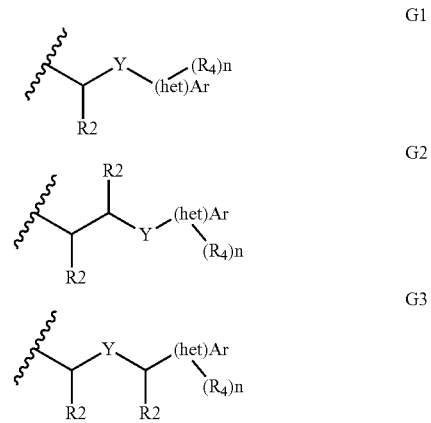

The integer number "n" is 0 (zero) to 2 (two);

R3 is selected from H, C1-5 alkyl, C2-5 fluoroalkyl, C1-3 alkyleneOC0-5 alkyl, C0-3 alkyleneNHC0-3 alkyl, C0-3 alkyleneN(C1-5 alkyl)2, in which the C1-5 alkyl may be the same or different, (CO)C1-5 alkyl, (CO)N(C0-5 alkyl)2, in which the C0-5 alkyl may be the same or different, and (CO)OC1-5 alkyl;

Two R2 or R2 and R3, if present, may optionally be connected to each other, or R2 or R3 may be connected to the carbon- or nitrogen-atom onto which the other R2 or R3 is attached in case the other R2 or R3 is hydrogen, by a bond replacing a hydrogen atom in each substituent to form part of a 5-membered or a 6-membered ring;

R4 is independently selected from C1-5 alkyl, C1-5 fluoroalkyl, halo, OH, NH2, C0-C3 alkylene phenyl, C0-C3 alkylene heteroaryl, C0-1 alkylene cyano, C0-3 alkyleneOC0-5 alkyl, C0-3 alkyleneNHC0-3 alkyl, C0-3 alkyleneN(C1-5 alkyl)2, in which the C1-5 alkyl may be the same or different, N(C4-5 alkylene), N-morpholino, CO2H, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)2, in which the C1-5 alkyl may be the same or different, CO-3 alkyleneC(O)N(C4-5 alkylene) and (CO)NH2;

as a free base, an acid in its non-charged protonated form or a pharmaceutically acceptable salt, solvate or solvate of a salt thereof and as a pure stereoisomer, a racemic-diastereomeric- or scalemic mixture;

As disclosed below, various embodiments of the present invent are drawn to compounds according to the general formula (I), as disclosed above, wherein the various generic groups (R1 to R4, G, Y and (het)Ar) are elaborately disclosed.

As disclosed above, R1 may be independently selected from H, fluoro, chloro and bromo. Although each of R1 may differ from the other, it is preferred if both R1 are the same. Further, both R1 may be chloro.

As disclosed above, Y may be selected from S and NR3.

According to a preferred embodiment, Y is S. Thioethers are preferred over corresponding ether analogs as they have longer retention time in the lungs, likely due to their greater lipophilicity and lower solubility (cf. Example FC1), and thus may provide longer duration of action and/or improved in vivo effect. Further, the metabolic profile for thioethers are different, and they are more rapidly eliminated systemically, likely due to the metabolic liability of the sulphur atom. While the properties of thioethers differ from the ones of corresponding ether analogs, thioethers was still unexpectedly found to be highly efficacious bronchodilators (cf. Biological example B1), having anti-inflammatory properties (cf. Biological example B2) in in vitro models. Importantly, thioethers was unexpectedly found to have higher in vivo bronchodilatory effect compared to a previously described tetrahydroquinoline cinnamide that act by a non-adrenergic and non-muscarinic bronchodilating mechanism (cf. Biological example B3) and which has has been reported as a drug candidate (cf. M. F. Dalence-Guzmán et al. in Bioorg. Med. Chem. Lett. 20 (2010) 4999-5003). All-in-all, thioethers were not only found to be equally acting to the corresponding ethers, but actually to have improved in vivo effect when administered via pulmonary route.

According to another embodiment Y is NR3.

In an embodiment wherein Y is NR3, R3 may selected from H, C1-5 alkyl, C2-5 fluoroalkyl, C1-3 alkyleneOC0-5 alkyl, C0-3 alkyleneNHC0-3 alkyl, C0-3 alkyleneN(C1-5 alkyl)2, in which the C1-5 alkyl may be the same or different, (CO)C1-5 alkyl, (CO)N(C0-5 alkyl)2, in which the C0-5 alkyl may be the same or different, and (CO)OC1-5 alkyl. Further, R3 may be selected from H, C1-5 alkyl and C2-3 alkyleneOH. R3 may also be H.

(het)Ar in G in formula (I) is a monocyclic aromatic ring, such as 5- or 6-membered heteroaryl or a benzene ring. Without limitations such 5- or 6-membered heteroaryls may be selected from pyrrole, furan, thiophen, thiazole, oxazole, triazole, pyridine, pyrimidine, pyrazine, oxadiazole and imidazole. The monocyclic aromatic ring may be substituted with a maximum of "n", wherein n" represents an integer number of 0 (zero) to 2, independently selected substituent (s) R4 at any substitutable ring atom. The integer number "n" may be 0 (zero) and if "n" is zero, then het(Ar) is unsubstituted. Further, "n" may be 1 or 2, if "n" is 1 or 2 then het(Ar) is substituted. If "n" is 2, then the two substituents R4 may be the same or different. Additionally, (het)Ar may represent both an aryl and a heteroaryl. Accordingly, het(Ar) may be selected from benzene, pyridine and pyrimidine. In one preferred embodiment het(Ar) is pyridine.

In one embodiment wherein "n" is 2, the two substituents R4 are different.

As disclosed above, R4 may be independently selected from C1-5 alkyl, C1-5 fluoroalkyl, halo, OH, NH2, C0-C3 alkylene phenyl, C0-C3 alkylene heteroaryl, C0-1 alkylene cyano, C0-3 alkyleneOC0-5 alkyl, C0-3 alkyleneNHC0-3 alkyl, C0-3 alkyleneN(C1-5 alkyl)2, in which the C1-5 alkyl may be the same or different, N(C4-5 alkylene), N-morpholino, CO2H, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)2, in which the C1-5 alkyl may be the same or different, C0-3 alkyleneC(O)N(C4-5 alkylene) and (CO)NH2.

In another embodiment, R4 may be independently selected from C1-5 alkyl, C1-5 fluoroalkyl, halo, phenyl, heteroaryl, cyano, OH, OC1-5 alkyl, NH2, NHC1-3 alkyl, N(C1-5 alkyl)2, in which the C1-5 alkyl may be the same or different, N(C4-5 alkylene) and N-morpholino. Further, R4 may preferably be independently selected from methyl, trifluoromethyl and fluoro.

In one embodiment two R2 or R2 and R3 are connected to each other, or R2 or R3 is connected to the carbon- or nitrogen-atom onto which the other R2 or R3 is attached if the other R2 or R3 is hydrogen, by a bond replacing a hydrogen atom in each substituent to form part of a 5-membered or a 6-membered ring. Non-limiting examples of such structures, in which one of the bonds, which could be regarded as the connecting bond and, is indicated with an arrow, are depicted below.

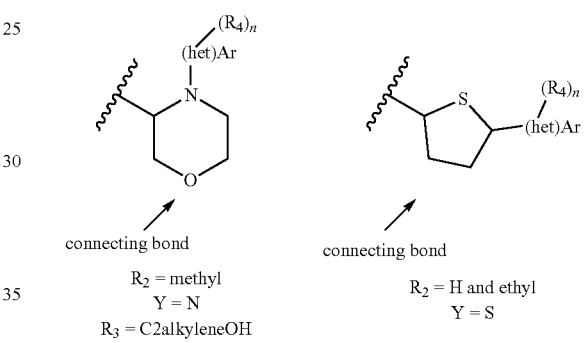

In one embodiment, wherein Y is NR3, R3 together with N and R2 may form part of a 5-membered or a 6-membered ring. Example 4 herein is one example within this embodiment.

In another embodiment two R2 or R2 and R3 are not connected to each other, whereby (het)Ar is more flexible with regard to the tetrahydroiosquinoline part of (I).

G in formula (I) may be selected from G1 to G3 as depicted above. In one embodiment G is G1.

R2 in G1 to G3 may be selected from H and C1-2 alkyl, such as methyl. In one embodiment R2 is hydrogen.

If R2 is C1-2 alkyl then the carbon atom bearing R2 will be a stereo center.

Embodiments of the present invention encompass compounds of formula (I) present in enantiomerically pure form, as well as compounds being present as racemic or scalemic mixtures. Further, embodiments of the present invention encompass compounds of formula (I) present as a pure diastereomer, as well as being present as mixtures of different diastereomers.

Similarly, if R2 is part of a 5-membered or a 6-membered ring then the carbon atom bearing R2 will be a stereo center. Embodiments of the present invention encompass compounds of formula (I) present in enantiomerically pure form, as well compounds being present as racemic or scalemic mixtures. Further, embodiments of the present invention encompass compounds of formula (I) present as a pure diastereomer, as well as being present as mixtures of different diastereomers.

In one embodiment R1 is chloro, Y is selected from S and NR3, preferably S, and (het)Ar is selected from benzene, pyridine and pyrimidine.

In one embodiment R1 is chloro, Y is S, (het)Ar is pyridine, R2 is H or methyl, "n" is 1 or 2 and R4 is selected from methyl, trifluoromethyl and fluoro.

In one embodiment, wherein (het)Ar is pyridine or benzene and "n" is at least 1, at least one of the substituents R4 is attached to the 3- or 4-position of (het)Ar relative to the attachement point of the linker comprising Y which according to this definition, is attached at position 1.

Furthermore, in an embodiment wherein (het)Ar is pyridine, the linker Y may be attached to the 2- or 3-position of (het)Ar relative to the nitrogen-atom of the pyridine, which according to this definition, is positioned at position 1.

In one embodiment, wherein (het)Ar is pyridine or benzene and "n" is 2, the two substituents R4 are attached in a 1,3-relationship, i.e. at the relative positions 1 and 3 of (het)Ar, with respect to each other.

In another embodiment, compounds according to the general formula (I) are selected from the group consisting of:

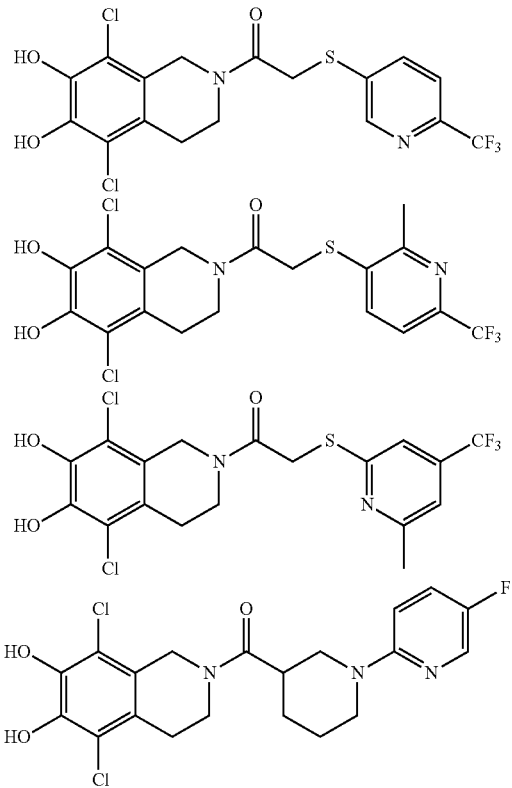

In another embodiment, compounds according to the general formula (I) are selected from the group consisting of:

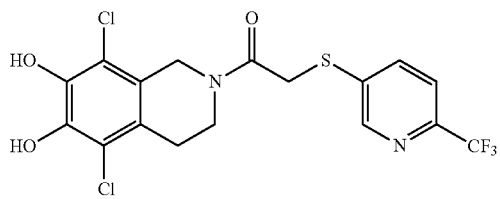

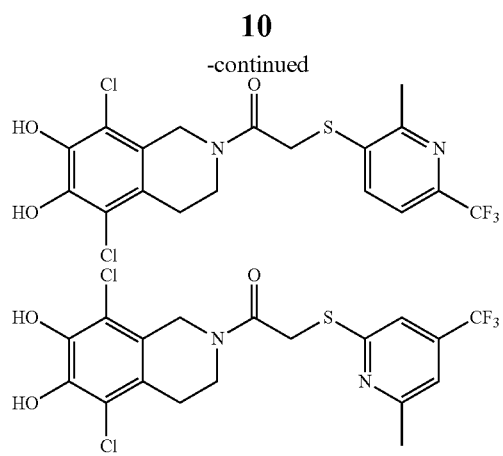

Another embodiment relates to a pharmaceutical composition, such as medicament, comprising a compound according to the various embodiments disclosed herein. Further, such a pharmaceutical composition may comprise a pulmonary drug. Such a pulmonary drug may be selected from pulmonary drugs wherein the principal mechanism of action of pulmonary drug is selected from the group consisting of β2-agonist, anticholinergicum and calcium antagonist, or wherein the pulmonary drug is a corticosteroid. Various examples of such pulmonary drugs are well known to the one skilled in the art.

According to another embodiment a compound or a pharmaceutical composition as disclosed herein may be used in therapy.

Furthermore, a compound or a pharmaceutical composition as disclosed herein may be used in the prevention and/or treatment of a disease or condition characterized by bronchoconstriction of the respiratory apparatus. In addition a compound or a pharmaceutical composition as disclosed herein may be used in the prevention and/or treatment of a disease or condition characterized by inflammation of the respiratory apparatus.

Diseases or conditions characterized by bronchoconstriction of the respiratory apparatus and/or by inflammation of the respiratory apparatus may be selected from the group consisting of asthma, chronic obstructive pulmonary disease, chronic bronchitis, emphysema, bronchiectasis, cystic fibrosis, bronchiolitis and bronchopulmonary dysplasia.

Another embodiment relates to a method of prevention and/or treatment of a disease or condition characterized by bronchoconstriction and/or inflammatory conditions of the respiratory apparatus, comprising administrering to a mammal, including man in need of such prevention and/or treatment, a therapeutically effective amount of compound as disclosed herein or a pharmaceutical composition comprising a therapeutically effective amount of a compound as disclosed herein. Further, such treatment and/or prevention may comprise the simultaneous or consecutive administration of at least one anti-asthmatic. If administered simultaneous or consecutive the administered dose of the anti-asthmatic may be 1 to 10 times less than the established therapeutically effective dose when administered alone for prevention or treatment of the same disease or condition. Further, if administered simultaneous or consecutive the administered dose of a compound as disclosed herein may be 1 to 10 times less than the established therapeutically effective dose when administered alone for prevention or treatment of the same disease or condition. When an anti-asthmatic used in such a method as disclosed above it may be selected from anti-asthmatics wherein the principal mechanism of action of the anti-asthmatic is selected from the group consisting of β2-agonist, anticholinergicum and calcium antagonist, or wherein the anti-asthmatic is a corticosteroid. Various examples of such anti-asthmatics are well known to the one skilled in the art.

According to another embodiment, a compound or a pharmaceutical composition as disclosed herein may be used in the prevention and/or treatment of a disease or condition characterized by systemic or respiratory vasoconstriction. Similarly, a compound or a pharmaceutical composition as disclosed herein may be used in a method of prevention and/or treatment of a disease or condition characterized by systemic or respiratory vasoconstriction. Such a method comprises administrering to a mammal, including man in need of such prevention and/or treatment, a therapeutically effective amount of a compound as disclosed herein or a pharmaceutical composition comprising a therapeutically effective amount of a compound as disclosed herein When used in herein, "prevent/preventing" should not be construed to mean that a condition and/or a disease never might occur again after use of a compound or pharmaceutical composition according to embodiments disclosed herein to achieve prevention. Further, the term should neither be construed to mean that a condition might not occur, at least to some extent, after such use to prevent said condition. Rather, "prevent/preventing" is intended to mean that the condition to be prevented, if occurring despite such use, will be less severe than without such use.

The usefulness of the compounds, as defined in the preceding embodiments, in treating, pretreating, revoking, mitigating, alleviating and/or preventing a condition of the respiratory apparatus characterized by bronchoconstriction, were evaluated in a complex and relevant in vitro model. The in vitro model was in accordance with the in vitro model disclosed in US 2006-0040254 A1 and Skogvall, S., Berglund, M., Dalence-Guzmán, M. F., Svensson, K., Jönsson, P., Persson, C. G. A and Sterner, O., Pulmonary Pharmacology and Therapeutics, vol 20:3, 2007, p. 273-280. All references disclosed herein are hereby incorporated in their entirety by reference.

In short, lung tissue was obtained from patients undergoing lobectomia or pulmectomia due to lung carcinoma. From the bronchus of this tissue were rectangular oblong preparations obtained. The contraction induced by inflammatory mediators, such as Leukotriene D4, histamine, prostaglandin D2 or acetylcholine, in the presence and absence of the compound to be evaluated, were compared.

Capsazepine, one of the first reported TRPV1-antagonists, has been shown to have an effect of human airways (Skogvall, S., Berglund, M., Dalence-Guzmán, M. F., Svensson, K., Jönsson, P., Persson, C. G. A and Sterner, O., Pulmonary Pharmacology and Therapeutics, vol 20:3, 2007, p. 273-280), but is also known to posses a range of other biological effects. Consequently capsazepine is not selective towards one target and accordingly its usefulness as a molecular tool has been questioned (Gunthorpe, M. J., Neurpharmacology, 2004, 46, 133).

The compounds synthesized as described below were all tested and shown to be at least comparably active to Capsazepine in the in vitro model referred to above.

According to one embodiment, preferred compounds according to any of the preceding embodiments are those being at least comparably active to Res-4-95, disclosed in Pulmonary Pharmacology & Therapeutics, 2007, 21(1), 125-133 as a potent analogue to Capsazepine, in the in vitro model referred to above.

Inflammation is closely associated with COPD. New drugs that reduce pulmonary inflammation by modulation of inflammatory pathways involving inflammatory mediators, such as leukotriene B4 (LTB4) and monocyte chemotactic protein-1 (MCP-1), is believed to provide effective and disease-modifying therapies and is therefore much desired (Friedman et al, Clinical Cornerstone, 2003, 5, 45-51).

MCP-1 attracts monocytes that can differentiate into macrophages. Macrophages are generally believed to be responsible for the continued protolytic activity in the lungs of COPD-patients, as well as driving the inflammatory process in the same by recruitment of neutrophils. The fact that increased levels of various inflammatory mediators, or associated receptors, correlates with the diagnosis of COPD, is indicative of their relevance in disease severity and progression. Comparative studies between COPD-patients and non-COPD subjects have, for example, shown that the former group has increased levels of MCP-1 in the sputum (Traves, L. S. et al, Thorax, 2002, 57, 590-595), increased mRNA expression of MCP-1 in lung tissue (Tomaki, M. et al, Pulmonary Pharmacology & Therapeutics, 2007, 20, 596-605), and increased lipopolysaccharide (LPS) stimulated release of MCP-1 from isolated blood monocytes (Aldonyte, R. et al, Respiratory Research, 2003.

LTB4 is an aracidonic acid metabolite involved in leukocyte recruitment. LTB4 is a potent chemoattractant and activator for neutrophils. The LTB4-receptors BLT1 and PPAR are upregulated in peripheral lung of COPD patients (Marian, E. et al, 2006, 129, 1523-1530). Higher sputum- (Profita, M. et al Allergy, 2005, 60, 1361-1369) and serum- (Segger, J. S. et al, Chest, 1991, 99, 289-291) concentrations of LTB4 is found in COPD-patients as compared to healthy controls. Reduction of serum inflammatory mediator levels, including LTB4-levels, by a dietary supplement containing omega-3 polyunsaturated fatty acids, correlated significantly to a clinical improvement in COPD-patients (Matsuyama, W. et al, Chest, 2005, 128, 3817-3827).

Accordingly, the anti-inflammatory effect, i.e. the usefulness in treating, pretreating, revoking, mitigating, alleviating and/or preventing an inflammation, such as an inflammation of the airways, of the compounds, as defined in the embodiments herein, may be assessed in an in vitro human peripheral blood mononuclear cell (PBMC) model. Further, the anti-inflammatory effect may be compared to the effect of dexamethasone, a known potent anti-inflammatory glucocorticoid.

According to one embodiment, preferred compounds according to any of the preceding embodiments are those being at least comparably active to dexamethasone in such an anti-inflammatory in-vitro model.

A protocol for such an anti-inflammatory in-vitro model is given herein.

A pharmaceutical composition, e.g. a medicament, as has been described herein above may further comprise pharmaceutically acceptable carriers, diluents, stabilisers and/or excipients.

"Pharmaceutically acceptable" means a carrier, stabiliser, diluent, excipient or other constituents that, at the dosage and concentrations employed, does not cause any unwanted effects in the patients to whom it is administered. Such pharmaceutically acceptable carriers, stabilisers, dilutents or excipients are well-known in the art, and examples of such are for example disclosed in Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

A pharmaceutical composition according embodiments herein may be administered to a patient in a pharmaceutically effective dose. By "pharmaceutically effective dose" is meant a dose that is sufficient to produce the desired effects in relation to the condition for which it is administered. The exact dose may be dependent on the activity of the compound, manner of administration, nature and severity of the disorder and/or disease and the general conditions, such as age and body weight of the patient.

According to one embodiment, a pharmaceutical composition according to embodiments herein may be administered alone or in combination with other therapeutic agents, such as anti-asthmatics. These agents may be incorporated as part of the same pharmaceutical composition or may be administered separately. It is well known in the art that a combination of mechanistically unrelated therapeutic agents in the same medicament may have beneficial effects in the treatment of conditions or diseases characterized by bronchoconstriction, as described in, for example, M. F. Fitzgerald and J. C. Fox, Drug Discovery Today, 2007, 12 (11/12), p. 472-478.

In one embodiment of the invention such other therapeutic agents to be administered in combination with a pharmaceutical composition according to embodiments herein are selected from therapeutic agents known to the one skilled in the art to prevent bronchoconstriction or revoke, fully or partly, any present bronchoconstriction. Examples of such agents are, but not limited to, β2-agonists, anticholinergics, calcium antagonists, and other agents suitable for the treatment of asthma and/or COPD and related diseases and/or disorders. Preferred agents in this aspect are β2-agonists and anticholinergics. Furthermore such other therapeutic agents to be administered in combination with pharmaceutical composition according to embodiments herein may also comprise therapeutic agents known to the one skilled in the art to be useful to treat, revoke, mitigate, alleviate or prevent inflammation associated with diseases and disorders of respiratory tract. Examples of such agents are corticosteroids.

When a compound according to embodiments disclosed herein is combined with at least another therapeutic agent, such as an anti-asthmatic, in a pharmaceutical composition, such as a medicament, a therapeutically effective dose of said pharmaceutical composition may comprise 1 to 10 times less than the respective established therapeutically effective dose of the components, i.e. a compound according to the invention and the therapeutic agent, when administered alone for prevention or treatment of the same disease or condition of each. Accordingly, by combining a compound according to embodiments disclosed herein with another therapeutic agent, such as an pulmonary drug, it may be possible to achieve synergistic effects compared to if only a compound according to the present invention, or the other therapeutic agent, were administrated alone. Furthermore, it may be possible to improve both the underlying cause, e.g. the inflammation, and the clinical signs, e.g. airflow obstruction and exacerbations.

A method to treat, revoke, mitigate, alleviate or prevent bronchoconstriction and/or an inflammatory condition in a mammal, such as a human being, in need thereof, by the administration of a compound or pharmaceutical composition, such as a medicament, according to embodiments disclosed herein may also include the simultaneous or consecutive administration a therapeutic agent, such as an anti-asthmatic. In such a method the therapeutically effective dose of said compound, medicament or pharmaceutical composition and said therapeutic agent may comprise 1 to 10 times less than the respective established therapeutically effective dose when administered alone for prevention or treatment of the same disease or condition. The advantages of such co-administration are discussed above.

A pharmaceutical composition according to embodiments disclosed herein may be administered through different routes such as, but not limited to, intravenously, intraperitonealy, intramuscularly, intranasaleously, subcutaneously, sublingually, rectally, orally or through inhalation or insufflation.

Particular suitable formulations of pharmaceutical compositions as disclosed herien are formulations suitable to be taken orally or to be administered through inhalation or insufflation.

Administration by inhalation or insufflation will allow a high proportion of the delivered dose to reach the site of action, that is, the bronchi and the lung in general. Furthermore the systemic effects may be lower if the medicament is administrated through inhalation or insufflation compared to other administration routes.

Inhalation may be by the oral or the nasal route. Conventional pulmonary applicators may be employed, such as pressurized spray containers comprising suitable propellants for aerosols and powder spray devices for preparations in form of fine powders. Pharmaceutical compositions suitable for administration by the inhalation or insufflation route are known in the art. The compound may be dissolved in a suitable vehicle or employed as a fine powder, such as a micronized powder of a medium particle size from about 2 μm to about 20 μm. An indicated daily dose for administration by inhalation may be 10 times lower than the corresponding oral dose. Satisfactory doses, preferably metered by using a device capable of metering, or by single doses of predetermined size, may easily be determined by experimentation.

Compounds according to embodiments disclosed herein may also be useful in treatment or prevention of hypertension. In the treatment of conditions or diseases characterized by hypertension, by employment of the compounds of the present invention, oral administration is the preferred route of administration.

In addition to their use in therapeutic medicine, compounds according to formula I may also be useful as pharmacological tools in the development and standardisation of in vitro and in vivo test systems for the evaluation of other compounds with similar activity. Furthermore, compounds of formula I may be used as molecular probes to identify and/or locate the target of their action, such as a target within the airways, as well as employed as a diagnostic tool for diagnosis of a disease or condition in vivo, ex vivo or in vitro, or as synthetic precursors to such probes. Molecular probes of formula I may include reactive, labeled, i.e. compounds of formula I wherein one or several of the composing atoms have been enriched with a radioactive isotope or by other means detectable, such as fluorescent compounds, as is well known to the one skilled in the art.

Methods of Preparation

Other embodiments of the present invention relates to processes for preparing a compound according to formula I as a free base, acid, or salts thereof. Further, additionally embodiments relate to synthetic intermediates, which are useful in the synthesis of a compound of formula I as a free base, acid, or salts thereof. Specific and generic examples of such intermediates are given below. Further, such intermediates may include compounds according to formula I, which may be used to produce another compound according to formula I.

Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are well known within the art. Further such procedures and groups are described in the literature, such as in "Protective Groups in Organic Synthesis", 3rd ed., T. W. Green, P. G. M. Wuts, Wiley-Interscience, New York (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Examples of transformations are given below, and it is to be understood that the described transformations are not limited only to the generic groups or substituents for which the transformations are exemplified.

References and descriptions on other suitable transformations are for example given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry well known to the one skilled in the art, such as "March's Advanced Organic Chemistry", 5th ed., M. B. Smith, J. March, John Wiley & Sons (2001) or, "Organic Synthesis", 2nd ed., M. B. Smith, McGraw-Hill, (2002).

Techniques for purification of intermediates and final products include for example, straight and reversed phase chromatography on column or rotating plate, recrystallisation, distillation and liquid-liquid or solid-liquid extraction, which will be readily understood by the one skilled in the art.

The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures.

The terms "flash chromatography" or "flash column chromatography" shall mean preparative chromatography on silica using an organic solvent, or mixtures thereof, as mobile phase.

Abbreviations aq. aqueous;
tBuOK potassium tert-butoxide;
CDI 1,1'-carbonyl diimidazole;
Cbz carbobenzyloxy;
DMAP 4-dimethylaminopyridine;
DMF N,N-dimethylformamide;
EDC HCl N-(3-dimethylaminopropyl)-N'-ethyl-carbodiimide hydrochloride;
EtOAc ethyl acetate;
EtOH ethanol;
Et₃N triethyl amine;

Et₂O diethylether;
h hour(s);
HBr hydrobromic acid;
HCl hydrochloric acid;
HOBt 1-hydroxybenzotriazole hydrate;
H₂SO₄ sulphuric acid;
MeOH methanol;
MgSO₄ magnesium sulphate;
NaHCO₃ sodium bicarbonate;
NaOH sodium hydroxide;
on over night;
PEPPSI-IPr 1,3-diisopropylimidazol-2-ylidene) (3-chloropyridyl)palladium(II) dichloride;
pet. ether petroleum ether;
rt room temperature;
SiO₂ silica gel;
THF tetrahydrofurane;
TLC thin layer chromatography;
TMS tetramethylsilane;
quant. quantitatively.

Methods of Preparation of Final Compounds of Formula I (Scheme 1 and 2)

Scheme 1

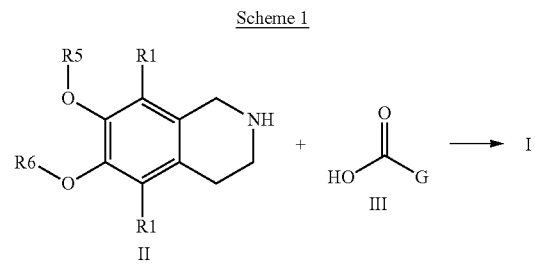

Formation of compounds of formula I, may be accomplished by coupling of II and III (wherein depicted groups R1 and G are the same as the corresponding groups in compounds of formula I) under standard amide coupling conditions, such as in the presence of N-(3-dimethylaminopropyl)-N'-ethyl-carbodiimide hydrochloride, 1-hydroxybenzotriazole hydrate, 4-dimethylaminopyridine and cesium carbonate (see for example Toftered et al., SYNLETT, 2004, 2517-2520) or 1,1'-carbonyl diimidazole in combination with 1-hydroxybenzotriazole hydrate or 2-hydroxy-5-nitropyridine (Dunn et al., Org. Proc. Res. Dev., 2005, 9, 956-961). The N-acylation of II may be accompanied by competing O-acylation when one or both of the substituents R5 and R6 are hydrogens. Thus, it is preferred to protect the corresponding phenolic moieties with suitable protective groups, such as methyl, before N-acylation of II. Methyl protective groups may be introduced by treatment with a methyl halide in the presence of a base according to standard procedures, and removed after the N-acylation by treatment with, for example, hydrogen bromide or boron tribromide (Hall et al., Bioorg. Med. Chem, 2005, 13, 1409-1413). Other aromatic methyl ethers, optionally present in the molecule, are then simultaneously cleaved off.

As an alternative approach towards compounds of formula I, precursors to carboxylic acids of general formula III may be coupled to the O-methylated version of amine II (i.e. R5=R6=Me) as depicted in scheme 2 (PG represents a suitable amine protective group such as tert-butoxy carbonyl) using, for example, the same standard peptide reagents as exemplified above. Chemical modifications of the acid-precursor, when already attached to II, can then be performed via, for example, conjugation of an amine such as VI with an aromatic ring, (het)Ar. This reaction may be performed with traditional methods such as nucleophilic aromatic substitution or newer transition-metal catalysed methods such as the Buchwald-Hartwig reaction. The latter reaction may be performed with the catalyst PEPPSI-IPr to give intermediate VII. As the last step towards I, the catechol moiety may then be demethylated, according to procedures discussed above.

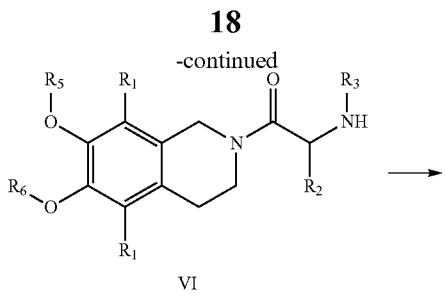

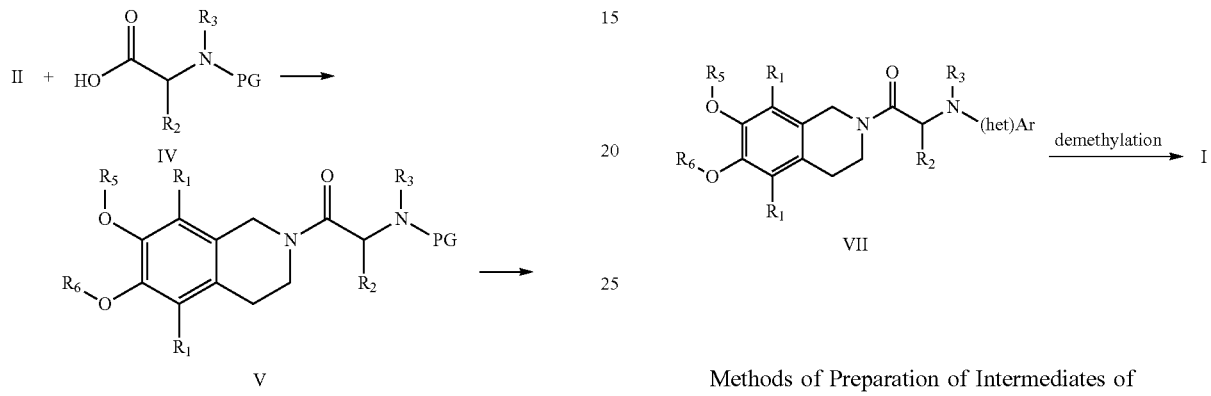

Methods of Preparation of Intermediates of Formula II (Scheme 3)

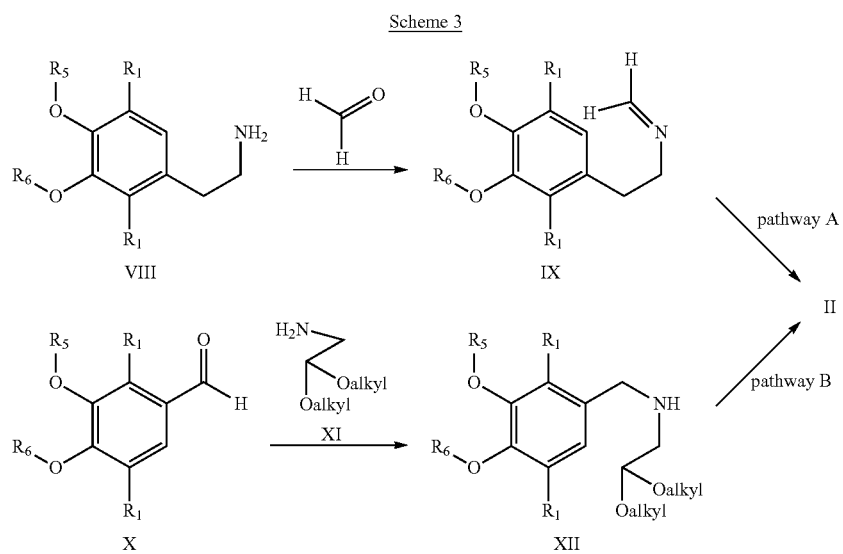

Examples of two non-limiting methods or the preparation of intermediates of formula II, by assembly of the tetrahydroisoquinoline ring, include pathway A and pathway B as depicted in scheme 3.

The synthesis according to pathway A involves a Pictet-Spengler reaction in which readily available phenylethylamine VIII is reacted with formaldehyde to yield IX, followed by cyclisation under acidic conditions (Yokoyama et al., J Org Chem, 1999, 64, 611-617; for a modified procedure allowing cyclisation onto electron poor aromatics see for example Stokker et al., Tetrahedron Lett, 1996, 37, 5453-5456).

The synthesis corresponding to pathway B involves a Pomerantz-Fritsch reaction under reductive conditions in which readily available benzaldehydes X are reacted with aminoacetals XI (depicted "alkyl" is preferably short alkyls such as ethyl) to yield XII, followed by cyclisation under acidic and reductive conditions to yield II (see for example: Bobbit et al., J Org Chem, 1965, 30, 2247-2250; Bobbit et al., J Org Chem, 1968, 33, 856-858).

Additional methods for the preparation of intermediates II include, for example, the direct introduction of the substituents R1 by electrophilic aromatic substitution, such as chlorination by treatment with sulphuryl chloride in acetic acid, or bromination as described in Okano et al., Tetrahedron, 2006, 128, 7136-7137.

Methods of Preparation of Intermediates of Formula III (Scheme 4)

benzophenone. Microwave heating was performed with an Emrys Smith Creator. HRMS (ESI) spectra were recorded with a micromass Q-TOF Micro spectrometer. NMR spectra (in CDCl3, CD3OD or DMSO-d6) were recorded on a Bruker DRX 400 or on a Bruker Ultrashield 400 spectrometer at 400 MHz. All chemical shifts are in ppm on the delta-scale (δ) relative to TMS using the residual CHCl3 peak in CDCl3, or the residual CD2HOD peak in CD3OD, or the residual CD3SOCD2H peak in (CD3)2SO as internal standard (7.26, 3.31 or 2.50 ppm respectively relative to TMS) and the fine splitting of the signals as appearing in the recordings (s: singlet, d: doublet, t: triplet, q: quartet, m: multiplet, br: broad signal). Flash chromatography was performed using 60 Å 35-70 µm Davisil silica gel. TLC analyses were made on Silica Gel 60 F254 (Merck) plates and visualised under a 254/365 nm UV-lamp.

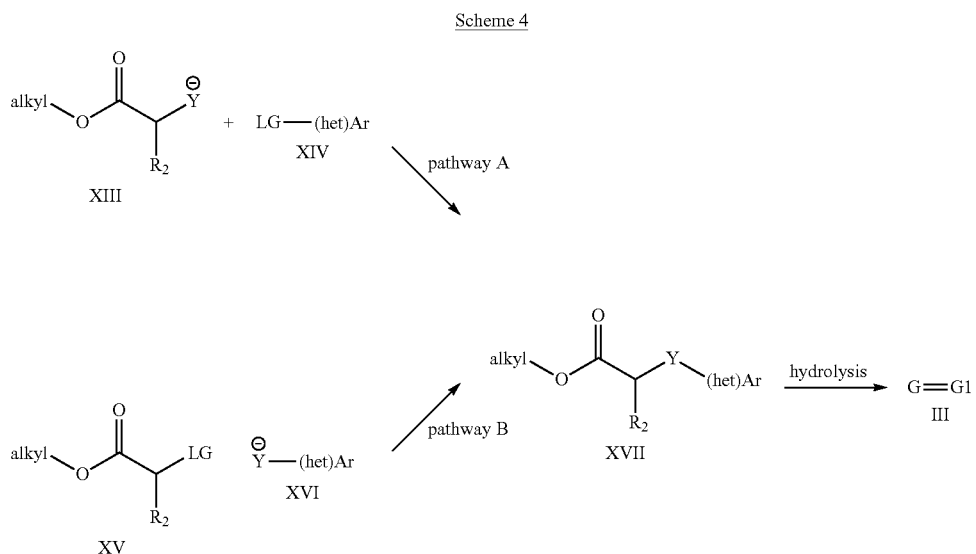

Scheme 4

Intermediates of formula III may, for example, be prepared via standard substitution reactions between readily available esters XIII or XV and heteroaryl-compounds such as XIV or XVI (depicted "alkyl" is preferably C1-C5 alkyls such as methyl, depicted LG may be iodo, bromo or chloro and depicted Y may be oxygen or sulfur), followed by hydrolysis with, for example, sodium hydroxide in methanol, as depicted in scheme 4. Which of the substitution pathways (A or B, Scheme 3) that is most suitable is much dependant on the nature and availability of the hetero aromatic compounds XIV and XVI as is readily understood by the one skilled in the art. Pathway A may be preferred in cases when the leaving group is positioned such, that it allows for direct substitution with reactive enough nucleophiles, as for example in the case of 2-halopyridines. Otherwise B is the preferred pathway.

Compound Examples

General Methods

All materials were obtained from commercial sources, unless stated otherwise, and were used without further purification unless otherwise noted. DMF was dried over molecular sieves (4 Å). THF was distilled from sodium and

Preparation of Intermediates

Below follows non-limiting examples on the synthesis of intermediates useful for the preparation of compounds of formula I.

5,8-Dichloro-6,7-dimethoxy-1,2,3,4-tetrahydroisoquinoline Hydrochloride

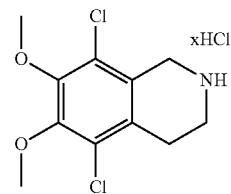 [SMILES: COc1c(Cl)c2c(c(Cl)c1OC)CNCC2]

6,7-Dimethoxy-1,2,3,4-tetrahydroisoquinoline hydrochloride (200 mg, 0.870 mmol) was suspended in glacial acetic acid (5 mL) and sulphuryl chloride (154 µL, 1.92 mmol) was added slowly. The resulting mixture was stirred at rt for 3 h and then evaporated to give the title compound (quant.) as a yellowish mass. $^1$H NMR (CD$_3$OD) δ 4.35 (br s, 2H), 3.90 (br d, 6H), 3.50 (br, 2H), 3.05 (br, 2H).

5,8-Dichloro-6,7-dihydroxy-1,2,3,4-tetrahydroisoquinoline hydrobromide

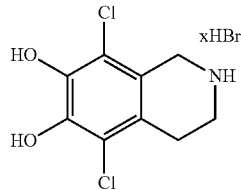 [SMILES: Oc1c(O)c(Cl)c2c(c1Cl)CCNC2]

5,8-Dichloro-6,7-dimethoxy-1,2-tetrahyroisoqnoline hydrochloride (1.0 g, 3.35 mmol) was suspended in aqueous HBr (48%, 10 mL) and refluxed for 5 h before evaporation. The remaining residue was evaporated twice from toluene to give 1.05 g (quant.) of the title compound as a pale solid. $^1$H NMR (CD$_3$OD) δ 6.60 (s, 1H) 6.57 (s, 1H) 4.26 (s, 2H) 3.50 (t, 2H, J=6 Hz) 3.01 (t, 2H, J=6 Hz).

6-(trifluoromethyl)pyridine-3-thiol

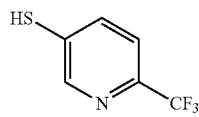

A solution of sodium nitrite (213 mg, 3.08 mmol) in water (620 µL) was slowly added to a suspension of 6-(trifluoromethyl)pyridine-3-amine (500 mg, 3.08 mmol) in conc. HCl (525 µL) and ice (620 mg) at 0° C. After five minutes of stirring at 0° C. a solution of potassium ethyl xanthate (593 mg, 3.70 mmol) in EtOH/water (1/1, 2 mL) was added and the resulting yellow slurry was heated at 50-55° C. for 30 minutes. Then the reaction mixture was allowed to cool to rt and was then diluted with water (10 mL) and Et$_2$O (10 mL). The phases were separated and the water phase was extracted with Et$_2$O (2×10 mL). The combined organics were washed with brine (10 mL) and dried (MgSO$_4$). After filtration and evaporation, the crude material (659 mg) was dissolved in EtOH (8 mL) and potassium hydroxide (735 mg) was added. The resulting mixture was heated at 90° C. for two hours and was then allowed to cool to rt. The reaction mixture was then filtered and the filtrate was acidified with citric acid, before being diluted with Et$_2$O. The organic phase was washed with brine and dried (MgSO$_4$). After filtration and evaporation of the solvent, the crude was dried under vacuum at 45° C. over night. The title compound (150 mg) was obtained as a yellow crude solid, which was not purified further but used directly in the next step. $^1$H NMR (CDCl$_3$) δ 8.80 (br s, 1H) 7.99 (br d, J=8.4 Hz, 1H9 7.66 (br d, J=8.4 Hz).

2-Methyl-6-(trifluoromethyl)nicotinonitrile

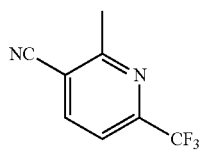

(E)-4-ethoxy-1,1,1-trifluorobut-3-en-2-one (Pal, M.; Khanna, I.; Subramanian, V.; Padakanti, S.; Pillarisetti, S. WO 2006058201 A2) (8.0 g, 47.6 mmol) and (E)-3-aminobut-2-enenitrile (3.9 g, 47.6 mmol) were dissolved in acetonitrile (40 mL). The resulting solution was heated at 80° C. for 20 hours, where after it was allowed to cool to rt. A yellow solid precipitated and after further cooling on an ice-water bath, the solid was collected via filtration and then dried under vacuum. The obtained title compound (1.32 g, 7.09 mmol, 15%) was used directly in the next step. $^1$H NMR (CD$_3$OD) δ 8.35-8.00 (br s, 1H) 6.19 (d, J=6.8 Hz, 1H) 2.33 (s, 3H).

2-Methyl-6-(trifluoromethyl)nicotinic Acid

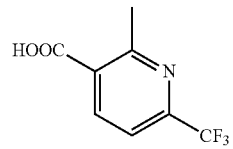

2-Methyl-6-(trifluoromethyl)nicotinonitrile (1.0 g, 5.4 mmol) was added to a solution of sodium hydroxide (2.2 g, 54 mmol) in EtOH/water (10 mL, 1/1). The resulting mixture was heated at 100° C. for one hour and was then allowed to cool to rt. The volatiles were evaporated, the residue poured into water (10 mL) and the water phase extracted with Et$_2$O (2×10 mL) to remove organic impurities. The water phase was acidified to pH 5-6 using 1M HCl aqueous solution and was then extracted with EtOAc (2×15 mL). The organic phase was washed with water (10 mL) and brine (10 mL) and dried (MgSO$_4$). After filtration and evaporation the obtained title compound (870 mg, 4.24 mmol, 79%) was used directly in the next step. $^1$H-NMR (CD$_3$OD) δ 8.45 (d, J=8.0 Hz, 1H) 7.72 (d, J=8.0 Hz, 1H) 2.84 (s, 3H).

Benzyl 2-methyl-6-(trifluoromethyl)pyridin-3-ylcarbamate

Diphenylphosphoryl azide (1.0 mL, 4.67 mmol), triethyl amine (766 µL, 5.51 mmol) and benzyl alcohol (658 µL, 6.36 mmol) were added to a suspension of 2-methyl-6-(trifluoromethyl)nicotinic acid (870 mg, 4.24 mmol) in toluene (10 mL). The resulting mixture was heated at 70° C. for one hour and then at 100° C. for one hour, after which it was allowed to cool to rt. The reaction mixture was poured into saturated NaHCO$_3$ aqueous solution (10 mL) and was extracted with EtOAc (3×10 mL). Combined organics were washed with saturated NaHCO$_3$ aqueous solution (10 mL), water (10 mL) and brine (10 mL) and dried (MgSO$_4$). After filtration and evaporation of solvent, the crude was purified by column chromatography (SiO$_2$, petroleum ether/EtOAc 95/5) to give the title compound (1.01 g, 3.26 mmol, 78%) as an off-white solid. $^1$H-NMR (CDCl$_3$) 8.49 (d, J=8.8 Hz, 1H) 7.55 (d, J=8.4 Hz, 1H) 7.45-7.39 (m, 5H) 6.68 (br s, 1H) 5.25 (s, 2H) 2.56 (s, 3H).

2-Methyl 6-(trifluoromethyl)pyridin-3-amine

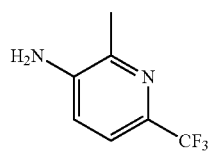

Ammonium formiate (4.6 g) and 10% Pd/C (228 mg) were added to a solution of benzyl 2-methyl-6-(trifluoromethyl)pyridin-3-ylcarbamate (1.01 g, 3.26 mmol) in EtOH (100 mL). The resulting mixture was heated at 100° C. for 40 minutes after which it was allowed to cool to rt. The reaction mixture was filtered through a small pad of Celite before it was concentrated. The residue was obtained in saturated NaHCO$_3$ aqueous solution (20 mL) and EtOAc (20 mL). The phases were separated and the water phase was extracted with EtOAc (2×20 mL). The combined organics were washed with brine (20 mL) and dried (MgSO$_4$). After filtration and evaporation the title compound (547 mg, 3.11 mmol, 95%) was assessed pure enough to be used directly in the next step. $^1$H-NMR (CDCl$_3$) δ 7.35 (d, J=8.4 Hz, 1H) 6.96 (d, J=8.0 Hz, 1H) 3.94 (br s, 2H) 2.46 (s, 3H).

O-ethyl S-2-methyl-6-trifluoromethyl)pyridin-3-yl Carbonodithioate

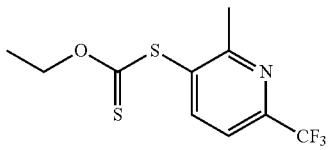 [SMILES: CCOC(=S)Sc1ccc(C(F)(F)F)nc1C]

A solution of sodium nitrite (216 mg, 3.14 mmol) in water (2 mL) was slowly added to a suspension of 2-methyl 6-(trifluoromethyl)pyridin-3-amine (500 mg, 2.84 mmol) in 2M HCl aqueous solution (9.6 mL) and water (7.9 mL) at 0° C. After two hours of stirring at 0° C. the bright yellow reaction mixture was added to a solution of potassium ethyl xanthate (547 mg, 3.41 mmol) in water (2 mL) at 65° C. The resulting mixture was kept at this temperature for 15 minutes before it was allowed to cool to rt. The water phase was extracted with EtOAc (2×10 mL), then neutralized with 1M NaOH aqueous solution and again extracted with EtOAc (2×10 mL). Combined organics were washed with brine (10 mL) and dried (MgSO$_4$). After filtration and evaporation the crude material (659 mg) was purified by column chromatography (SiO$_2$, petroleum ether/EtOAc 99/1) to give the title compound (180 mg, 0.64 mmol, 23%) as a yellow oil, together with considerable amounts of 2-methyl-6-(trifluoromethyl)pyridin-3-thiol (299 mg, 1.06 mmol, 37%, yellow solid). $^1$H NMR (CDCl$_3$) title compound δ 7.95 (d, J=8.0 Hz, 1H) 7.58 (d, J=8.0 Hz, 1H) 4.64 (q, J=7.2 Hz, 2H) 2.73 (s, 3H) 1.37 (t, J=7.2 Hz, 3H).

2-Methyl-6-(trifluoromethyl)pyridin-3-thiol

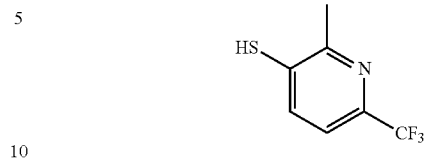

1M NaOH aqueous solution (6.4 mL) was added to a solution of O-ethyl S-2-methyl-6-(trifluoromethyl)pyridin-3-yl carbonodithioate (180 mg, 0.64 mmol) in EtOH (6.4 mL) at rt. The resulting mixture was stirred at rt over night. Then the reaction mixture was acidified to pH 4-5 using 1M HCl aqueous solution. The water phase was extracted with EtOAc (3×8 mL) and combined organics were washed with brine (10 mL) and dried (MgSO$_4$). After filtration and evaporation of the solvent the title compound (113 mg, 0.58 mmol, 91%, yellow solid) was obtained pure enough to be used directly in the next step. $^1$H-NMR (CD$_3$OD) δ 7.46 (d, J=8.4 Hz, 1H) 7.21 (d, J=8.0 Hz, 1H) 2.45 (s, 3H).

General Procedure for the Reaction of Phenols and Aromatic Thiols (Thiophenols) of General Formula XVI (Scheme 4) with Methyl 2-Bromoacetate Methyl 2-bromoacetate (2 eq.) and potassium carbonate (2 eq.) were added to a solution of the respective phenol/aromatic thiol (1 eq.) in acetone (5 mL/mmol) at rt. The resulting mixture was heated at reflux until starting materials were consumed (as indicated by TLC) and was then allowed to cool to rt. The solvent was evaporated and the residue obtained in water and EtOAc. The phases were separated and the water phase was extracted twice with EtOAc. The combined organics were washed with water and brine and dried (MgSO$_4$). After filtration and evaporation the crude was purified via column chromatography.

Methyl 2-(6-(trifluoromethyl)pyridin-3-ylthio)acetate

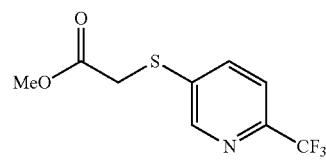

SiO$_2$, pet. ether/EtOAc 92/8. Colourless oil. Yield: 48%. $^1$H NMR (CDCl$_3$) δ 8.67 (br s, 1H) 7.88-7.86 (m, 1H) 7.62-7.601 (m, 1H) 3.76 (s, 3H) 3.74 (s, 2H).

Methyl 2-(2-methyl-6-(trifluoromethyl)pyridine-3-ylthio)acetate

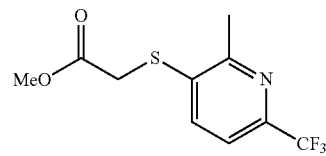

SiO$_2$, pet. ether/EtOAc 9/1. Light orange liquid. Yield: 73%. $^1$H NMR (CDCl$_3$) δ 7.47 (d, J=8.4 Hz, 1H) 7.02 (d, J=8.8 Hz, 1H) 4.73 (s, 2H) 3.82 (s, 3H) 2.59 (s, 3H).

Methyl 2-(6-methyl-4-(trifluoromethyl)pyridin-2-ylthio)acetate

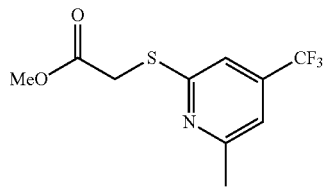 [SMILES: COC(=O)CSc1cc(C(F)(F)F)cc(C)n1]

2-chloro-6-methyl-4-(trifluoromethyl)pyridine (166.4 mg, 0.85 mmol), methyl thioglycolate (167.4 μL, 1.87 mmol) and caesium carbonate (554.4 mg, 1.70 mmol) were suspended in anhydrous DMF (3.0 ml) and placed in a screw cap pressure tube. The tube was sealed and the mixture was heated to 130° C. for one h. Water (20 mL) was added and the product extracted with EtOAc. Combined organics were dried (MgSO$_4$), filtered and concentrated. Purification was done by column chromatography (SiO$_2$, pet. ether/EtOAc (95/5→90/10) affording 45.0 mg (20%) of the title compound as a colorless oil. $^1$H NMR (CDCl$_3$) 7.25 (bs, 1H) 7.04 (bs, 1H) 3.99 (s, 2H) 3.76 (s, 3H) 2.54 (s, 3H).

General Procedure for Methyl Ester Hydrolysis to Yield Carboxylic Acids of General Formula III (Scheme 4)

To a solution of a carboxylic acid of general formula III (1.0 eq.) in MeOH (4 mL/mmol) was added 1M NaOH aqueous solution (3 eq.). The resulting solution was stirred at rt on. The volatiles were evaporated and the resulting water phase was acidified to pH 4-5 using 1M HCl aqueous solution. The acidic water phase was then extracted three times with EtOAc and combined organics were washed with water and brine and dried (MgSO$_4$). After filtration and evaporation the carboxylic acids were obtained pure enough to be used directly in the next step.

2-(6-(Trifluoromethyl)pyridin-3-ylthio)acetic Acid

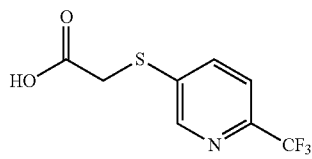 [SMILES: O=C(O)CSc1ccc(C(F)(F)F)nc1]

Brownish oil. Yield: 72%. $^1$H NMR (CD$_3$OD) δ 8.64 (br s, 1H) 8.01-7.98 (m, 1H) 7.71-7.69 (m, 1H) 3.90 (s, 2H).

2-(2-Methyl-6-(trifluoromethyl)pyridin-3-ylthio)acetic Acid

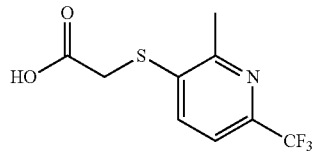 [SMILES: Cc1nc(C(F)(F)F)ccc1SCC(=O)O]

Light yellow solid. Yield: 87%. $^1$H NMR (CD$_3$OD) δ 7.58 (d, J=8.8 Hz, 1H) 7.36 (d, J=8.8 Hz, 1H) 4.86 (s, 2H) 2.53 (s, 3H).

2-(6-Methyl-4-(trifluoromethyl)pyridin-2-ylthio)acetic Acid

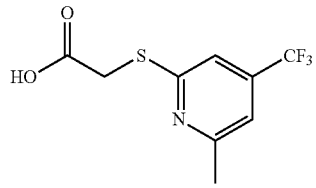 [SMILES: Cc1cc(C(F)(F)F)cc(SCC(=O)O)n1]

Yellowish solid. Yield: 68%. $^1$H NMR (CD$_3$OD) δ 7.37 (br s, 1H) 7.20 (br s, 1H) 4.00 (s, 2H) 2.56 (s, 3H).

tert-Butyl 3-(5,8-dichloro-6,7-dimethoxy-1,2,3,4-tetrahydroisoquinoline-2-carbonyl)piperidine-1-carboxylate

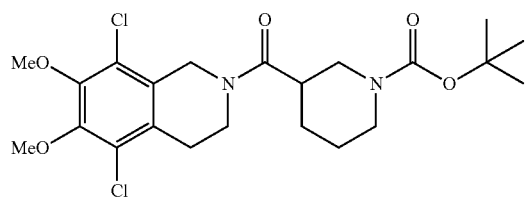 [SMILES: COc1c(Cl)c2c(c(Cl)c1OC)CN(C(=O)C1CCCN(C(=O)OC(C)(C)C)C1)CC2]

5,8-Dichloro-6,7-dimethoxy-1,2,3,4-tetrahydroisoquinoline (400 mg, 1.53 mmol), EDC HCl (626 mg, 3.26 mmol), N-Boc-nipecotic acid (549 mg, 2.39 mmol), HOBt (333 mg, 2.18 mmol), DMAP (531 mg, 4.35 mmol) and cesium carbonate (1.42 g, 4.35 mmol) were suspended in DMF (40 ml) and stirred at rt for 20 h. The reaction was diluted with water (200 ml) and extracted with EtOAc (3×80 ml). Combined organics were washed with NaHCO$_3$ (2×100 ml, sat aq.), dried over MgSO$_4$, filtered and evaporated. The product was purified by column chromatography (SiO$_2$, pet. ether/EtOAc, 1/1) to give 456 mg (63%) of the title compound as a clear, sticky mass. $^1$H NMR (CDCl$_3$) rotameric mixture δ 4.77-4.55 (br, 2H) 4.20-4.05 (br, 2H) 3.82 (s, 6H) 4.81-4.70 (br, 2H) 3.96-3.85 (br, 2H) 3.85-3.75 (br, 1H) 3.75-3.63 (br, 2H) 2.94-2.83 (br, 2H) 2.80-2.62 (br, 2H) 1.46 (s, 9H).

5,8-Dichloro-6,7-dimethoxy-3,4-dihydroisoquinolin-2(1H)-yl-(piperidin-3-yl)methanone

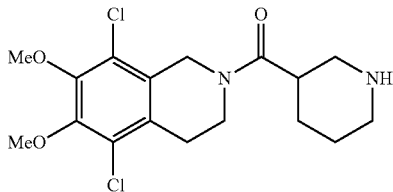 [SMILES: COc1c(Cl)c2c(c(Cl)c1OC)CN(C(=O)C1CCCNC1)CC2]

tert-Butyl 3-(5,8-dichloro-6,7-dimethoxy-1,2,3,4-tetrahydroisoquinoline-2-carbonyl)piperidine-1-carboxylate (100 mg, 0.21 mmol) was dissolved in dichloromethane (10 ml). To this were added triethylsilane (102 µl, 0.63 mmol) and trifluoroacetic acid (235 µl, 3.17 mmol) and the resulting solution was stirred at rt for 15 h before evaporation. The residue was dissolved in chloroform (40 ml), washed with NaOH (40 ml, 2 M aq), dried (MgSO$_4$), filtered and evaporated. The product was purified by column chromatography using dichloromethane/MeOH/Et$_3$N (18/2/1) as eluent to give 69 mg (88%) of the title compound as a yellowish residue. $^1$H NMR (CDCl$_3$) rotameric mixture δ 4.70 (ma)(s, 2H) 4.62 (mi)(s, 2H) 3.91 (s, 6H) 3.82 (mi)(m, 2H) 3.74 (ma)(br t, 2H) 4.20-4.05 (br, 2H) 3.82 (s, 6H) 3.11-2.98 (br m, 2H) 2.95-2.86 (br, 2H) 2.84-2.76 (br, 2H) 2.74-2.61 (br, 2H) 2.17-2.00 (br, 2H) 1.95-1.83 (br, 1H) 1.79-1.69 (br, 2H) 1.61-1.50 (br, 1H).

5,8-Dichloro-6,7-dimethoxy-3,4-dihydroisoquinolin-2(1H)-yl-(1-(5-fluoropyridin-2-yl)piperidin-3-yl)methanone

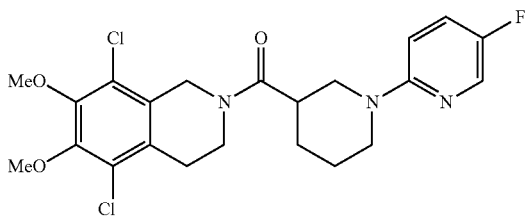 [SMILES: COc1c(Cl)c2c(c(Cl)c1OC)CN(C(=O)C1CCCN(c3ccc(F)cn3)C1)CC2]

5,8-Dichloro-6,7-dimethoxy-3,4-dihydroisoquinolin-2(1H)-yl-(piperidin-3-yl)methanone (69 mg, 0.18 mmol), 2-bromo-5-fluoropyridine (37 mg, 0.21 mmol) and tBuOK (28 mg, 0.25 mmol) were suspended in 1,2-dimethoxyethane (2.5 ml). The suspension was degassed with nitrogen before addition of PEPPSI-IPr (6 mg, 0.008 mmol). The reaction flask was sealed and stirred at rt for 4 h, then at 50° C. for 20 h. The resulting mixture was diluted with EtOAc (20 ml), washed with water (20 ml), dried (MgSO$_4$), filtered and evaporated. The product was purified by column chromatography (SiO$_2$, pet. ether/EtOAc, 3/1→2/1) to give 25 mg (30%) of the title compound. $^1$H NMR (CDCl$_3$) rotameric mixture δ 8.10 (s, 1H) 7.25 (s, 1H) 6.68 (br t, 1H) 4.85-4.70 (m, 2H) 4.43 (br t, 1H) 4.10 (br d, 1H) 3.83 (s, 6H) 3.74 (m, 1H) 3.05-2.77 (br m, 6H) 1.98-1.83 (br, 2H) 1.80-1.74 (br, 1H) 1.69-1.57 (br, 2H) 1.49-1.40 (br, 1H) 1.38-1.24 (br, 2H)1.15-1.07 (br, 1H).

Preparation of Final Compounds

The following non-limiting examples of compounds of formula I did all show less than 60% remaining contraction, at a concentration of 10 µM, of human bronchiols after LTD4 induced contraction according to the method described herein.

General Procedure for the Synthesis of Compounds of Formula I (Scheme 1, R1=Cl, R5=R6=H) Via Amide Coupling Using CDI and a Catalyst CDI (1.1 eq.) was added to a solution of a carboxylic acid of general formula III (1.0 eq.) in dry THF (20 mL/mmol). The resulting suspension was heated at reflux until the carboxylic acid was consumed (as indicated by TLC). The reaction mixture was then allowed to cool to rt and 5,6-dichloro-6,7-dihydroxy-1,2,3,4-tetrahydroisoquinoline hydrobromide (1.0 eq.) and a catalyst (as indicated for each case, 0.25 eq.) were added. The reaction mixture was again heated at reflux until starting materials were consumed (as indicated by TLC). After the reaction mixture had reached rt the solvent was removed and the residue obtained in water and EtOAc. The phases were separated and the water phase extracted twice with EtOAc. Combined organics were washed with water and brine and dried (MgSO$_4$). After filtration and evaporation, the crude was purified by column chromatography to yield the final compound.

Example 1

1-(5,8-Dichloro-6,7-dihydroxy-3,4-dihydroisoquinolin-2(1H)-yl)-2-(6-(trifluoromethyl)pyridin-3-ylthio)ethanone

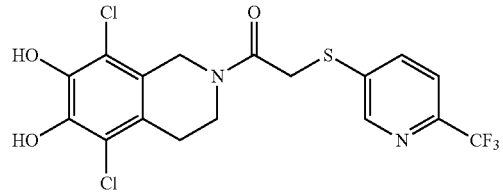

Catalyst: 2-hydroxy-5-nitropyridine. SiO$_2$, pet. ether/EtOAc 6/4. Yellow solid. Yield: 44%. $^1$H NMR (CD$_3$OD) rotameric mixture δ 8.68 (ma)(d, J=2.4 Hz, 1H) 8.61 (mi)(d, J=2.4 Hz, 1H) 8.05 (ma)(dd, J=1.6, 8.4 Hz, 1H) 7.96 (mi)(dd, J=2.0, 8.4 Hz, 1H) 7.71 (ma)(d, J=8.4 Hz, 1H) 7.65 (mi)(d, J=8.4 Hz, 1H) 4.67 (mi)(s, 2H) 4.62 (ma)(s, 2H) 4.22 (ma)(s, 2H9 4.19 (mi)(s, 2H) 3.84 (ma)(t, J=6.0 Hz, 2H) 3.78 (mi)(t, J=6.0 Hz, 2H) 2.92 (ma)(t, J=6.0 Hz, 2H) 2.69 (mi)(t, J=6.0 Hz, 2H).

Example 2

1-(5,8-Dichloro-6,7-dihydroxy-3,4-dihydroisoquinolin-2(1H)-yl)-2-(2-methyl-6-(trifluoromethyl)pyridin-3-ylthio)ethanone

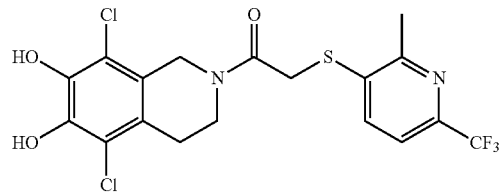 [SMILES: Cc1nc(C(F)(F)F)ccc1SCC(=O)N1CCc2c(Cl)c(O)c(O)c(Cl)c2C1]

Catalyst: HOBt. SiO$_2$, pet. ether/EtOAc 7/3→1/1. Yield: 21%. $^1$H NMR (CD$_3$OD) rotameric mixture δ 7.59-7.56 (m, 1H) 7.39-7.37 (m, 1H) 5.14 (ma)(s, 2H) 5.13 (mi)(s, 2H) 4.65 (s, 2H) 3.83 (mi)(t, J=6.2 Hz, 2H) 3.78 (ma)(t, J=6.0 Hz, 2H) 2.93 (ma)(t, J=5.8 Hz, 2H) 2.78 (mi)(t, J=6.0 Hz, 2H) 2.56 (ma)(s, 3H) 2.48 (mi)(s, 3H).

Example 3

1-(5,8-Dichloro-6,7-dihydroxy-3,4-dihydroisoquinolin-2(1H)-yl)-2-(6-methyl-4-(trifluoromethyl)pyridin-2-ylthio)ethanone

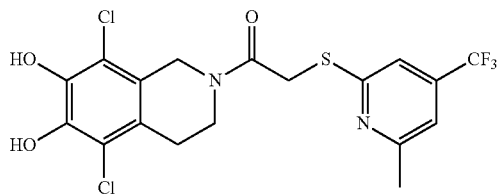 [SMILES: Cc1cc(C(F)(F)F)cc(SCC(=O)N2CCc3c(Cl)c(O)c(O)c(Cl)c3C2)n1]

Catalyst: HOBt. SiO$_2$, dichloromethane/MeOH 95/5. Yield: 49%. $^1$H NMR (CD$_3$OD) rotameric mixture δ 7.40 (ma)(s, 1H) 7.37 (mi)(s, 1H) 7.18 (bs, 1H) 4.77 (mi)(s, 2H) 4.66 (ma)(s, 2H) 4.31 (bs, 2H) 3.93 (mi)(bs, 2H) 3.82 (ma)(t, J=6.0 Hz, 2H) 2.95 (ma)(bs, 2H) 2.76 (mi)(t, J=5.6 Hz, 2H) 2.44 (ma)(s, 3H) 2.40 (mi)(s, 3H).

Example 4

(5,8-Dichloro-6,7-dihydroxy-3,4-dihydroisoquinolin-2(1H)-yl)(1-(5-fluoropyridin-2-yl)piperidin-3-yl)methanone

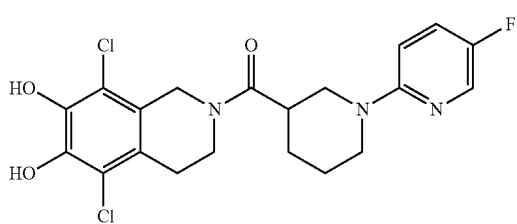 [SMILES: O=C(C1CCCN(c2ccc(F)cn2)C1)N1CCc2c(Cl)c(O)c(O)c(Cl)c2C1]

5,8-Dichloro-6,7-dimethoxy-3,4-dihydroisoquinolin-2 (1H)-yl-(1-(5-fluoropyridin-2-yl)piperidin-3-yl)methanone (25 mg, 0.053 mmol) was suspended in dichloromethane (5 ml) and cooled to 0° C. Boron tribromide (159 μl, 0.159 mmol, 1 M) was added slowly and the resulting mixture was stirred at rt for 20 h. The reaction was quenched with MeOH (1 ml) and evaporated. The residue was dissolved in MeOH (5 ml) and neutralized with NaHCO$_3$ (45 mg, 0.53 mmol) before evaporation. The product was purified by column chromatography (SiO$_2$, CH$_2$Cl$_2$/MeOH 20/0→20/1→20/2) to give 9 mg (38%) of the title compound as a yellowish residue. $^1$H NMR (CDCl$_3$) rotameric mixture δ 7.99 (d, J=7 Hz, 1H) 7.36 (m, 1H) 6.84 (m, 1H) 4.77-4.56 (m, 1H) 4.43-4.33 (m, 1H) 4.15-4.08 (m, 1H) 3.95-3.83 (m, 2H) 3.17-3.10 (m, 2H) 3.03-2.84 (br m, 4H) 2.74 (br t, 1H) 1.98-1.91 (br, 1H) 1.88-1.71 (br, 2H) 1.68-1.54 (br, 1H) 1.35-1.23 (m 4H) 1.16-1.03 (m, 1H).

Physical-Chemical Example

Example FC1—Solubility

The usefulness and suitability of the compounds, as defined in the embodiments herein, as inhaled drug products for treating, revoking, mitigating, alleviating and/or preventing a condition of the respiratory apparatus characterized by bronchoconstriction, are dependent on their physical chemical properties and in particular solubility.

The solubilities of 1-(5,8-Dichloro-6,7-dihydroxy-3,4-dihydroisoquinolin-2(1H)-yl)-2-(6-(trifluoromethyl)pyridin-3-ylthio)ethenone (example 1) and the known compound 1-(5,8-Dichloro-6,7-dihydroxy-3,4-dihydroisoquinolin-2 (1H)-yl)-2-(6-(trifluoromethyl)pyridine-3-yloxy)ethanone in phosphate buffer (pH 7.4) were determined.

Briefly, 1 mg of the study compounds were weighted into glass vials (two replicates). 2 ml of pH 7.4 phosphate buffer was added into the vials and vials were then agitated (1300 rpm) 20 hours at 37° C. Samples were filtrated using 0.45 μm PVDA syringe filters before analysis. 10 μg/ml and 500 μg/ml standard solutions in acetonitrile:ultra-pure water were prepared using 10 mM DMSO-stock solution. Samples and standards were analyzed from glass vials. The samples were analyzed using UPLC/PDA immediately after preparation. A Waters Acquity ultra high-performance liquid chromatographic (UPLC) system with autosampler, vacuum degasser, photo-diode-array detector (Acquity PDA) and column oven was used.

TABLE 1

| Solubility in phosphate buffer (pH 7.4) | |
|---|---|
| Compound | Solubility (μg/ml) |
| Example 1 | 16.6 |
| 1-(5,8-Dichloro-6,7-dihydroxy-3,4-dihydroisoquinolin-2(1H)-yl)-2-(6-(trifluoromethyl)pyridine-3-yloxy)ethanone | 76.7 |

As can be seen in Table 1, example 1 displays lower solubility in water compared to the close analog 1-(5,8-Dichloro-6,7-dihydroxy-3,4-dihydroisoquinolin-2(1H)-yl)-2-(6-(trifluoromethyl)pyridine-3-yloxy)ethanone. It is believed that lower solubility in water will increase the lung residence time after inhalation, thereby increasing the efficacy of the treatment.

BIOLOGICAL EXAMPLES

Biological Example B1

The usefulness of the compounds, as defined in the embodiments herein, in treating, revoking, mitigating, alleviating and/or preventing a condition of the respiratory apparatus characterized by bronchoconstriction, were evaluated in a complex and relevant in vitro model, which is described in US 2006-0040254 A1 and Skogvall, S., Berglund, M., Dalence-Guzmán, M. F., Svensson, K., Jönsson, P., Persson, C. G. A and Sterner, O., Pulmonary Pharmacology and Therapeutics, vol 20:3, 2007, p. 273-280. All references disclosed herein are hereby incorporated in their entirety by reference.

In short, lung tissue was obtained from patients undergoing lobectomia or pulmectomia due to lung carcinoma. From the bronchus of this tissue were rectangular oblong preparations obtained. The contraction induced by inflammatory mediators, such as Leukotriene D4, histamine, prostaglandin D2 or acetylcholine, in the presence and absence of the compound to be evaluated, were compared.

The remaining contraction, after pre-treatment with various compound examples at a concentration of 10 µM, of human bronchiols after Leukotriene D4 (10 nM) induced contraction according to the in vitro method described herein above are tabulated below.

TABLE 2

Remaining contraction after Leukotriene D4 (10 nM) induced contraction

| Compound | Remaining contraction (%) |
|---|---|
| Example 1 | 7 |
| Example 2 | 14 |
| Example 3 | 16 |
| Example 4 | 51 |

As can be seen from the data above, the brochorelaxing activity follows structure activity relationship established in Bioorganic & Medicinal Chemistry Letters 20 (2010) 4999-5003, with regards to the heteroaryl moiety and it is expected that compounds belonging to structure I will have desirable bronchorelaxing properties in vivo as confirmed in Biological example B3 (cf. below).

Biological Example B2—Human Peripheral Blood Mononuclear Cell (PBMC) In Vitro Model Cryopreserved PBMC's (SeraCare, #72001) are thawed, washed with culture media (RPMI-1640 from Invitrogen, #61870-036+10% heat inactivated fetal bovine serum from Invitrogen, #10082-147+100 U/ml penicillin+100 µg/ml streptomycin) and tested for viability using Trypan blue (PBMC viability=96%). Cells are then resuspended to 1×106 cells/ml in culture media and 0.5 ml plated into 24 well culture plates (5×105 cells/well) before incubation for 30 minutes at 37° C. with 5% C02 prior to addition of a compound to be assessed (10 µM) or dexamethasone (1 µM). One hour thereafter, LPS (0.1 µg/ml, *Salmonella abortus equi*, Sigma, #L1887) are added and the cells are incubated for another 24 h before collection of the cell culture supernatants, which are assayed for the presence of MCP-1 and LTB4.

MCP-1 levels are quantified employing a Luminex-based assay according the manufacturer's instructions. Data are collected using a Luminex 100 (Luminex Corporation, Austin, Tex.). Standard curves are generated using a 5-parameter logistic curve fitting equation weighted by 1/y (StarStation V 2.0; Applied Cytometry Systems, Sacramento, Calif.). Each sample reading are interpolated from the appropriate standard curve. Calculated concentrations are multiplied by the appropriate dilution factor when necessary.

LTB4 levels are quantified by ELISA following the manufacturer's instructions. Absorbance readings are detected using a ThermoMax microplate reader (Molecular Devices). Standard curves are generated using a 4-parameter logistic curve fitting equation (SoftMax Pro 4.7.1; Molecular Devices). Each sample reading are interpolated from the appropriate standard curve. Duplicate interpolated sample values are averaged and standard deviations are calculated. Calculated concentrations are multiplied by the appropriate dilution factor.

The reults in lowering MCP-1 and LTB-4 levels compared to vehicle (negative control) and 1 µM dexamethasone (positive control) are given below.

TABLE 3

Reduction of LPS induced levels of MCP-1 and LTB-4

| Test item | MCP-1 reduction (%) | LTB-4 reduction (%) |
|---|---|---|
| Vehicle | 0 | 0 |
| Dexamethasone | 15.5 | 23.4 |
| Example 1 | 70.8 | 20.7 |

As can be seen in Table 3, Example 1 has a significant reduction of two relevant inflammatory markers (MCP-1 and LTB-4, respectively).

Biological Example B3—Evaluation of Inhibitory Effect on Carbamylcholine-Induced Bronchospasm in Anaesthesia Rats The bronchocondilatator effect of example 1 and (2E)-1-(5,8-dichloro-3,4-dihydro-6,7-dihydroxy-2(1H)-isoquinolinyl)-3-[6-(trifluoromethyl)-3-pyridinyl]-2-propen-1-one was evaluated using the Konzett-Rossler method (cf. Konzett H, Rössler R (1940) Versuchsanordung zu Untersuchungen an der Bronchialmuskulatur. Naunyn-Schmiedeberg's Arch Exp Path Pharmakol 192:71-74) in the anaesthetised rat following single intra-tracheal administration.

The study involved male Sprague Dawley rats, weighing between 291.1 g and 347.7 g on the day of the test.

Animals were put on to a water-only fast the day prior to the test. On the day of the test, animals were anaesthetised using sodium pentobarbital at a dose of 60 mg/kg by intraperitoneal route in a volume of 1 mL/kg, then at 2 mg/mL by the intravenous route at a rate of 10 mL/kg/hour throughout the test. The trachea was quickly cannulated to enable artificial respiration. The animals were ventilated with an air flow of approximately 1 mL per 100 g at a rate of 54 cycles/minute. Total pulmonary resistance was measured continuously using a pressure transducer, fitted to a side branch of the tracheal cannula. Arterial blood pressure and heart rate were obtained by placing the telemetric pressure sensor of telemetric transmitter HD-S11 in the carotid artery. A jugular vein was cannulated for the intravenous administration of carbamylcholine chloride. The temperature of the animal was kept between 36.0° C. and 39.3° C. using an electric blanket. At the end of the surgical phase, animals were pre-medicated with a solution of pancuronium bromide at 0.2 mg/mL by the intravenous route at a rate of 10 mL/kg/hour throughout the test to avoid spontaneous respiration. Ventilatory flow was adjusted in such way as to obtain a baseline stabilisation of the pulmonary pressure resistance between 6.5 to 10.5 mmHg (i.e. approximately between 10 to 15% of maximum pulmonary resistance). About 15 minutes after the end of the surgical phase and stabilisation of the pulmonary pressure signal, the animals were dosed with:

1. Example 1;
2. (2E)-1-(5,8-dichloro-3,4-dihydro-6,7-dihydroxy-2(1H)-isoquinolinyl)-3-[6-(trifluoromethyl)-3-pyridinyl]-2-propen-1-one; or
3. Their vehicle by intra-tracheal nebulization in a volume of 100 µl using a Microsprayer aerosolizer (Penncentury).

Thirty minutes later, carbamylcholine chloride at 275 µg/kg was administered using an infusion pump in a volume of 3.33 mL/kg over a 5-minute period. Total pulmonary resistance, mean, systolic and diastolic arterial blood pressure and heart rate were continuously recorded over the test.

Example 1 was formulated by dissolving 5.5 mg in 2015 μl vehicle (200 mM (2-hydroxypropyl)-β-cyclodextrin, 49 mM L-lysine, 6.2 mM L-ascorbic acid in MilliQ water).

(2E)-1-(5,8-Dichloro-3,4-dihydro-6,7-dihydroxy-2(1H)-isoquinolinyl)-3-[6-(trifluoromethyl)-3-pyridinyl]-2-propen-1-one was formulated by dissolving 5.8 mg in 22250 μl vehicle (200 mM (2-hydroxypropyl)-β-cyclodextrin, 49 mM L-lysine, 6.2 mM L-ascorbic acid in MilliQ water).

TABLE 4 bronchodilatory effect in vivo

| Treatment | Total pulmonary resistance increase from baseline post carbamylcholine chloride challenge (mmHg) | |
| --- | --- | --- |
| | Average | SEM |
| Vehicle | 6.06 | 0.77 |
| Example 1 | 2.33 | 1.08 |
| (2E)-1-(5,8-dichloro-3,4-dihydro-6,7-dihydroxy-2(1H)-isoquinolinyl)-3-[6-(trifluoromethyl)-3-pyridinyl]-2-propen-1-one | 2.86 | 0.27 |

Under the experimental conditions adopted, example 1 and (2E)-1-(5,8-dichloro-3,4-dihydro-6,7-dihydroxy-2(1H)-isoquinolinyl)-3-[6-(trifluoromethyl)-3-pyridinyl]-2-propen-1-one administered at 6 mM had a bronchodilatating effect on carbamylcholine chloride induced bronchoconstriction (as measured in a smaller increase in pulmonary resitance compared to vehicle). As can be seen from Table 4, the bronchodilatory effect in vivo of example 1 was greater than the effect of the previously described bronchodilator (2E)-1-(5,8-dichloro-3,4-dihydro-6,7-dihydroxy-2(1H)-isoquinolinyl)-3-[6-(trifluoromethyl)-3-pyridinyl]-2-propen-1-one.

The present invention shows that the subtle switch from oxygen (O) to sulphur (S) give the unexpected advantage of increasing bronchodilatory efficacy in vivo (cf. Table 4) while at the same time improving the physical-chemical property (cf. Example FC1).

The invention claimed is:

1. A compound according to formula I

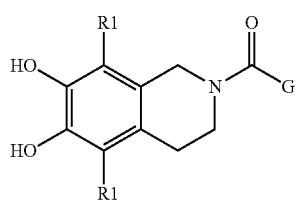

(I)

wherein
R1 is independently selected from H, fluoro, chloro and bromo;
G is selected from G1 to G3, wherein R2 is independently selected from H and C1-2 alkyl, Y is selected from S and NR3, (het)Ar is a monocyclic aromatic ring; said ring being substituted with a maximum of "n" independently selected substituent(s) R4 at any substitutable ring atom, wherein "n" represents an integer number;

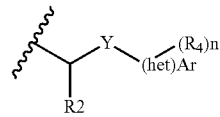

G1

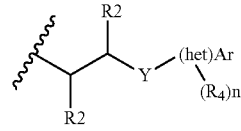

G2

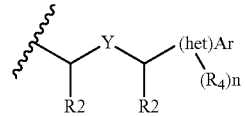

G3 the integer number "n" is 0 (zero) to 2 (two);
R3 is selected from H, C1-5 alkyl, C2-5 fluoroalkyl, C1-3 alkyleneOC0-5 alkyl, C0-3 alkyleneNHC0-3 alkyl, C0-3 alkyleneN(C1-5 alkyl)2, in which the C1-5 alkyl may be the same or different, (CO)C1-5 alkyl, (CO)N(C0-5 alkyl)2, in which the C0-5 alkyl may be the same or different, and (CO)OC1-5 alkyl;
two R2 or R2 and R3, if present, may optionally be connected to each other, or R2 or R3 may be connected to the carbon- or nitrogen-atom onto which the other R2 or R3 is attached in case the other R2 or R3 is hydrogen, by a bond replacing a hydrogen atom in each substituent to form part of a 5-membered or a 6-membered ring;
R4 is independently selected from C1-5 alkyl, C1-5 fluoroalkyl, halo, OH, NH2, C0-C3 alkylene phenyl, C0-C3 alkylene heteroaryl, C0-1 alkylene cyano, C0-3 alkyleneOC0-5 alkyl, C0-3 alkyleneNHC0-3 alkyl, C0-3 alkyleneN(C1-5 alkyl)2, in which the C1-5 alkyl may be the same or different, N(C4-5 alkylene), N-morpholino, CO2H, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)2, in which the C1-5 alkyl may be the same or different, C0-3 alkyleneC(O)N(C4-5 alkylene) and (CO)NH2;
as a free base, an acid in its non-charged protonated form or a pharmaceutically acceptable salt, solvate or solvate of a salt thereof and as a pure stereoisomer, a racemic-, diastereomeric- or scalemic mixture.

2. A compound according to formula I, wherein
R1 is chloro; and
(het)Ar is selected from benzene, pyridine and pyrimidine.

3. A compound according to claim 1, wherein the integer number n is 1 to 2.

4. A compound according to claim 1, wherein the integer number n is 0 (zero).

5. A compound according to claim 3, wherein R4 is selected from C1-5 alkyl, C1-5 fluoroalkyl, halo, phenyl, heteroaryl, cyano, OH, OC1-5 alkyl, NH2, NHC1-3 alkyl, N(C1-5 alkyl)2, in which the C1-5 alkyl may be the same or different, N(C4-5 alkylene) and N-morpholino.

6. A compound according to claim 5, wherein R4 is selected from methyl, trifluoromethyl, and fluoro.

7. A compound according to claim 1, wherein Y is S.

8. A compound according to claim 1, wherein Y is NR3 and R3 is selected from H, C1-5 alkyl and C2-3 alkyleneOH.

9. A compound according to claim 8, wherein R3 is H.
10. A compound according to claim 1, wherein G is G1.
11. A compound according to claim 1, wherein R2 is H.
12. A compound according to claim 1, wherein (het)Ar is pyridine.
13. A compound according to claim 12, wherein the compound is selected from:

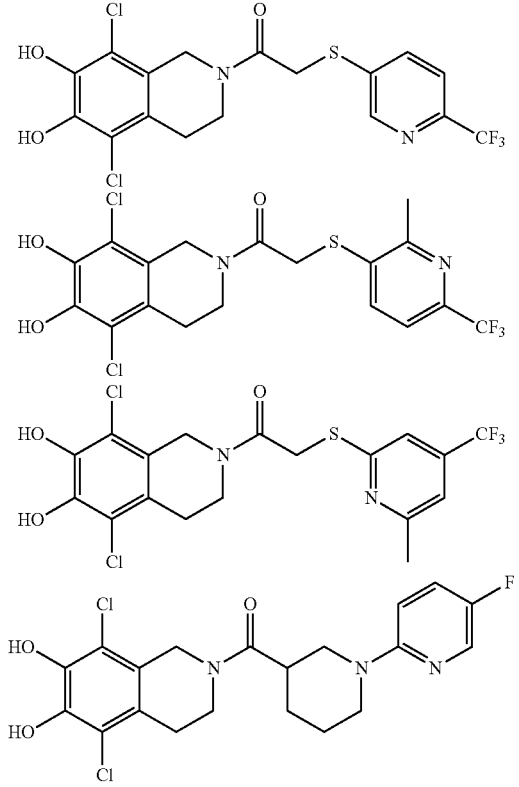

14. A pharmaceutical composition comprising a compound according to claim 1 and at least one pharmaceutically acceptable carrier.

15. A pharmaceutical composition according to claim 14, comprising a further pulmonary drug, wherein the principal mechanism of action of the further pulmonary drug is selected from the group consisting of β2-agonist, anticholinergic and calcium antagonist, or wherein the further pulmonary drug is a corticosteroid.

16. A method of prevention and/or treatment of a disease or condition characterized by bronchoconstriction and/or inflammatory conditions of the respiratory apparatus, comprising administering to a mammal in need of such prevention and/or treatment, a therapeutically effective amount of a compound according to claim 1.

17. The method according to claim 16 further comprising the simultaneous or consecutive administration of a therapeutically effective amount of a pulmonary drug.

18. The method according to claim 17, wherein the administered dose of the pulmonary drug is 1 to 10 times less than the established therapeutically effective dose when administered alone for prevention or treatment of the same disease or condition, and/or wherein the administered dose of a compound according to claim 1 is 1 to 10 times less than the established therapeutically effective dose when administered alone for the prevention or treatment of the same disease or condition.

19. The method according to claim 17, wherein the principal mechanism of action of the pulmonary drug is selected from the group consisting of β2-agonist, anticholinergic and calcium antagonist, or wherein the pulmonary drug is a corticosteroid.

20. A method of prevention and/or treatment of a disease or condition characterized by systemic or respiratory vasoconstriction, comprising administering to a mammal in need of such prevention and/or treatment, a therapeutically effective amount of a compound according to claim 1.

\* \* \* \* \*